(12) United States Patent
Kaufman et al.

(10) Patent No.: US 9,889,283 B2
(45) Date of Patent: Feb. 13, 2018

(54) DISPENSING APPLICATOR FOR FLUIDS

(71) Applicant: BIOMED PACKAGING SYSTEMS INC., Norwalk, CT (US)

(72) Inventors: Jack W. Kaufman, Merrick, NY (US); James Brown, Armonk, NY (US)

(73) Assignee: BIOMED PACKAGING SYSTEMS INC., Norwalk, CT (US)

( * ) Notice: Subject to any disclaimer, the term of this patent is extended or adjusted under 35 U.S.C. 154(b) by 151 days.

(21) Appl. No.: 14/732,983

(22) Filed: Jun. 8, 2015

(65) Prior Publication Data

US 2015/0273196 A1    Oct. 1, 2015

Related U.S. Application Data

(63) Continuation of application No. 13/306,681, filed on Nov. 29, 2011, now Pat. No. 9,073,382, which is a (Continued)

(51) Int. Cl.
*B43K 5/14* (2006.01)
*A61F 13/40* (2006.01)
(Continued)

(52) U.S. Cl.
CPC ........ *A61M 35/006* (2013.01); *A61M 35/003* (2013.01); *B43M 11/06* (2013.01)

(58) Field of Classification Search
CPC ........................... A61M 35/003; A61M 35/006
(Continued)

(56) References Cited

U.S. PATENT DOCUMENTS 3,063,084 A    11/1962   Marinus
3,271,810 A     9/1966   Raffe
(Continued)

FOREIGN PATENT DOCUMENTS

GB         2 185 880       8/1987
WO    WO 2004-062709      7/2004
(Continued)

OTHER PUBLICATIONS

EP Pat. Appln. No. 08 769 216.6, Supplementary EP Search Report, 10 pages, dated Feb. 17, 2012.
(Continued)

*Primary Examiner* — Jennifer C Chiang
(74) *Attorney, Agent, or Firm* — Andrew F. Young, Esq.; Lackenbach Siegel LLP

(57) ABSTRACT

A dispensing applicator may include a tubular container configured to contain a fluid. The container may include an inlet end and an outlet end, the container including a head member at the outlet end, the head member including a frangible region. A substantially rigid tongue may extend longitudinally through the frangible region. A fracture anvil may be engaged with the rigid tongue element and configured to fracture the frangible region without entirely separating the tongue from the head member. A cap may be secured to the inlet end of the container. A gasket placed between the inlet end and the cap, and the cap may be configured to deform the gasket such that the gasket fills any void remaining within the container after the container is filled with a predetermined volume of the fluid.

20 Claims, 20 Drawing Sheets

Related U.S. Application Data continuation of application No. 11/740,910, filed on Apr. 26, 2007, now Pat. No. 8,083,425, which is a continuation-in-part of application No. 11/138,142, filed on May 26, 2005, now Pat. No. 7,614,811.

(51) Int. Cl.
*A61M 35/00* (2006.01)
*B43M 11/06* (2006.01)

(58) Field of Classification Search
USPC .................................. 401/132–134
See application file for complete search history.

(56) References Cited

U.S. PATENT DOCUMENTS

| | | | | |
|---|---|---|---|---|
| 3,481,676 | A | * | 12/1969 | Schwartzman ........ A45D 34/04 401/134 |
| 3,777,949 | A | | 12/1973 | Chiquiari-Arias |
| 3,847,151 | A | * | 11/1974 | D'Alessandro ......... A47L 17/00 15/244.1 |
| 4,415,288 | A | * | 11/1983 | Gordon .................. A47K 7/028 401/132 |
| 4,732,287 | A | | 3/1988 | Bennett |
| 4,747,720 | A | | 5/1988 | Bellehumeur et al. |
| 5,090,832 | A | | 2/1992 | Rivera et al. |
| 5,434,660 | A | | 7/1995 | Wirt |
| 5,586,672 | A | | 12/1996 | Schneider et al. |
| 6,042,286 | A | | 3/2000 | Pazienza |
| 6,086,279 | A | | 7/2000 | Yen |
| 6,533,484 | B1 | * | 3/2003 | Osei .................... A61M 35/003 222/541.1 |
| 7,063,476 | B1 | | 6/2006 | Pinnix et al. |
| 7,252,091 | B1 | * | 8/2007 | Wayne ................... A45D 19/02 132/112 |
| 7,540,681 | B2 | * | 6/2009 | Cybulski ............. A61M 35/006 401/133 |
| 7,614,811 | B2 | | 11/2009 | Kaufman et al. |
| 7,946,779 | B2 | | 5/2011 | Kaufman et al. |
| 8,083,425 | B2 | | 12/2011 | Kaufman et al. |
| 8,186,897 | B2 | | 5/2012 | Kaufman et al. |
| 8,215,859 | B2 | | 7/2012 | Kaufman et al. |
| 8,511,923 | B2 | | 8/2013 | Kaufman et al. |
| 2004/0253039 | A1 | | 12/2004 | Stenton |
| 2006/0269355 | A1 | | 11/2006 | Kaufman |
| 2011/0142527 | A1 | | 6/2011 | Kaufman et al. |

FOREIGN PATENT DOCUMENTS

| | | |
|---|---|---|
| WO | WO 2006/041801 | 4/2006 |
| WO | WO 2007/018541 | 2/2007 |

OTHER PUBLICATIONS

EP Pat. Appln No. 08 769 216.6, Communication pursurant to Rules 70(2) and 70a(2) EPC, 1 page, dated Mar. 7, 2012.
PCT/US2008/061776, European Office Action dated Mar. 7, 2012, 11 pages.
International Search Report and Written Opinion, PCT/US2013/057017 dated Nov. 19, 2013, 19 pages.
Utility U.S. Appl. No. 12/596,103, filed Oct. 15, 2009.
Utility U.S. Appl. No. 13/601,755, filed Aug. 31, 2012.
PCT Appln. Serial No. PCT/US08/61776 filed Apr. 28, 2008.
EPC Appln. Serial No. 8769216.6 filed Apr. 28, 2008.
Utility U.S. Appl. No. 13/485,013, filed May 31, 2012.
Utility U.S. Appl. No. 13/946,009, filed Jul. 19, 2013.
Utility U.S. Appl. No. 14/068,905, filed Oct. 31, 2013.
PCT Appln. Serial No. PCT/US13/57017 filed Aug. 28, 2013.
Utility U.S. Appl. No. 13/971,425, filed Aug. 20, 2013.
Utility U.S. Appl. No. 13/306,681, filed Nov. 29, 2011.

\* cited by examiner

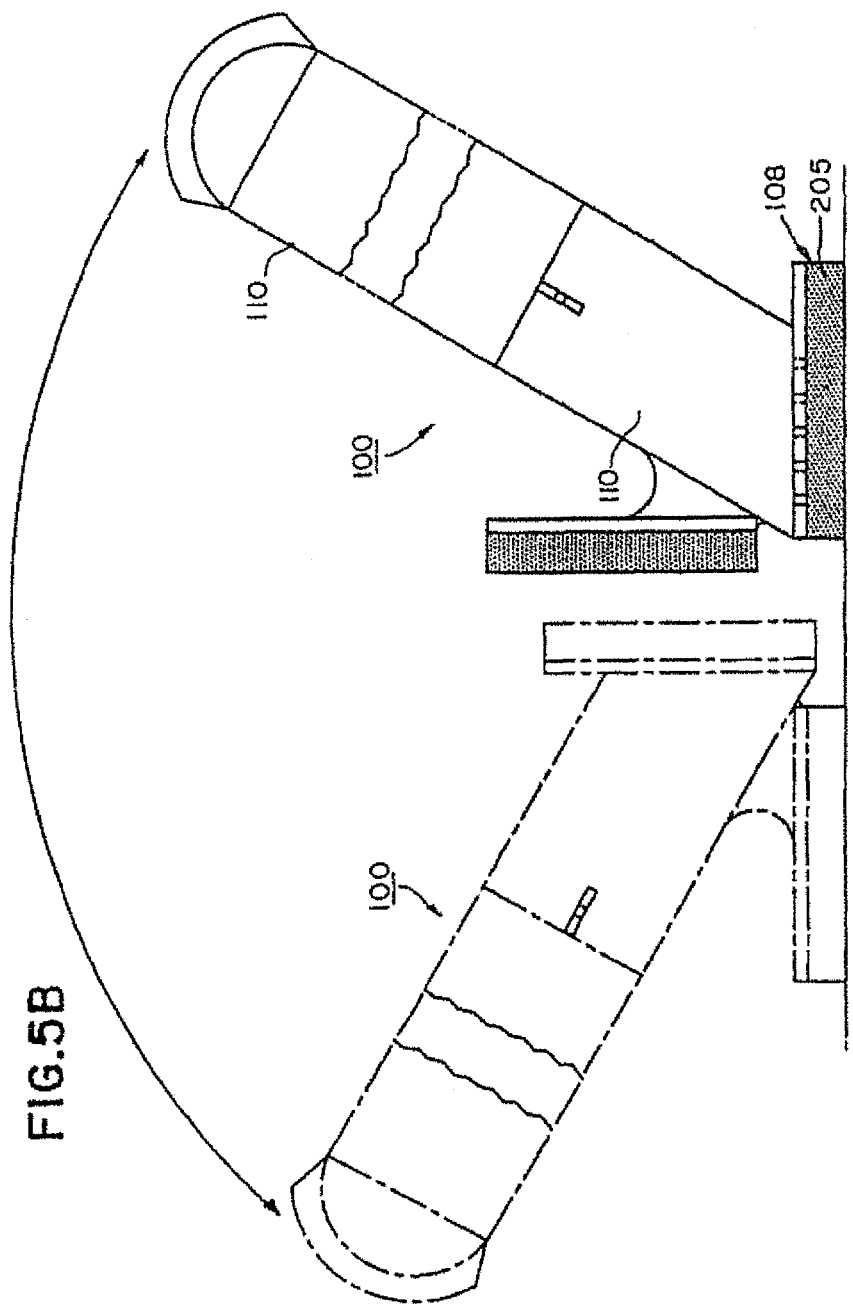

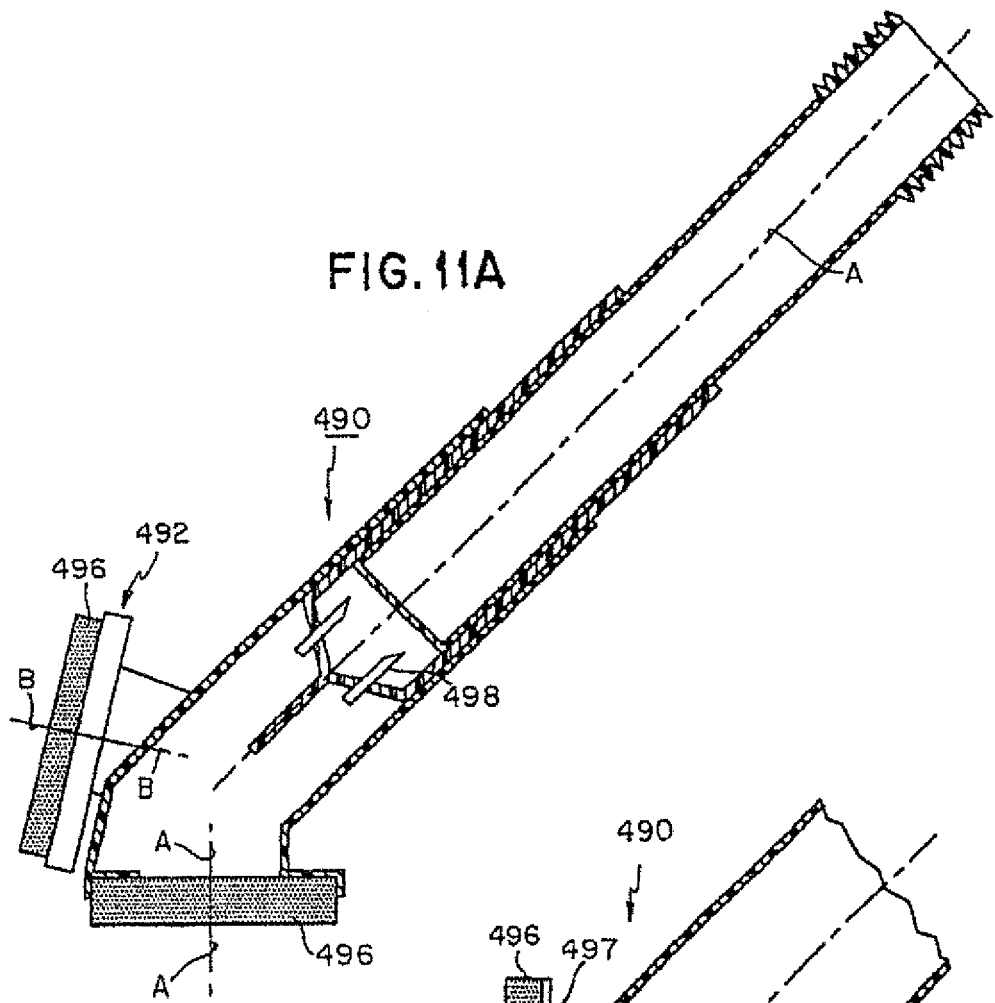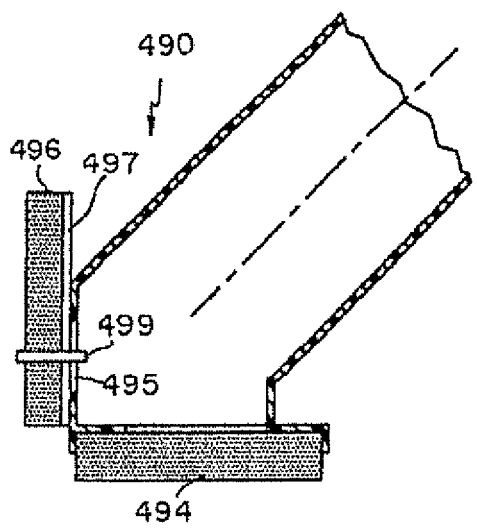

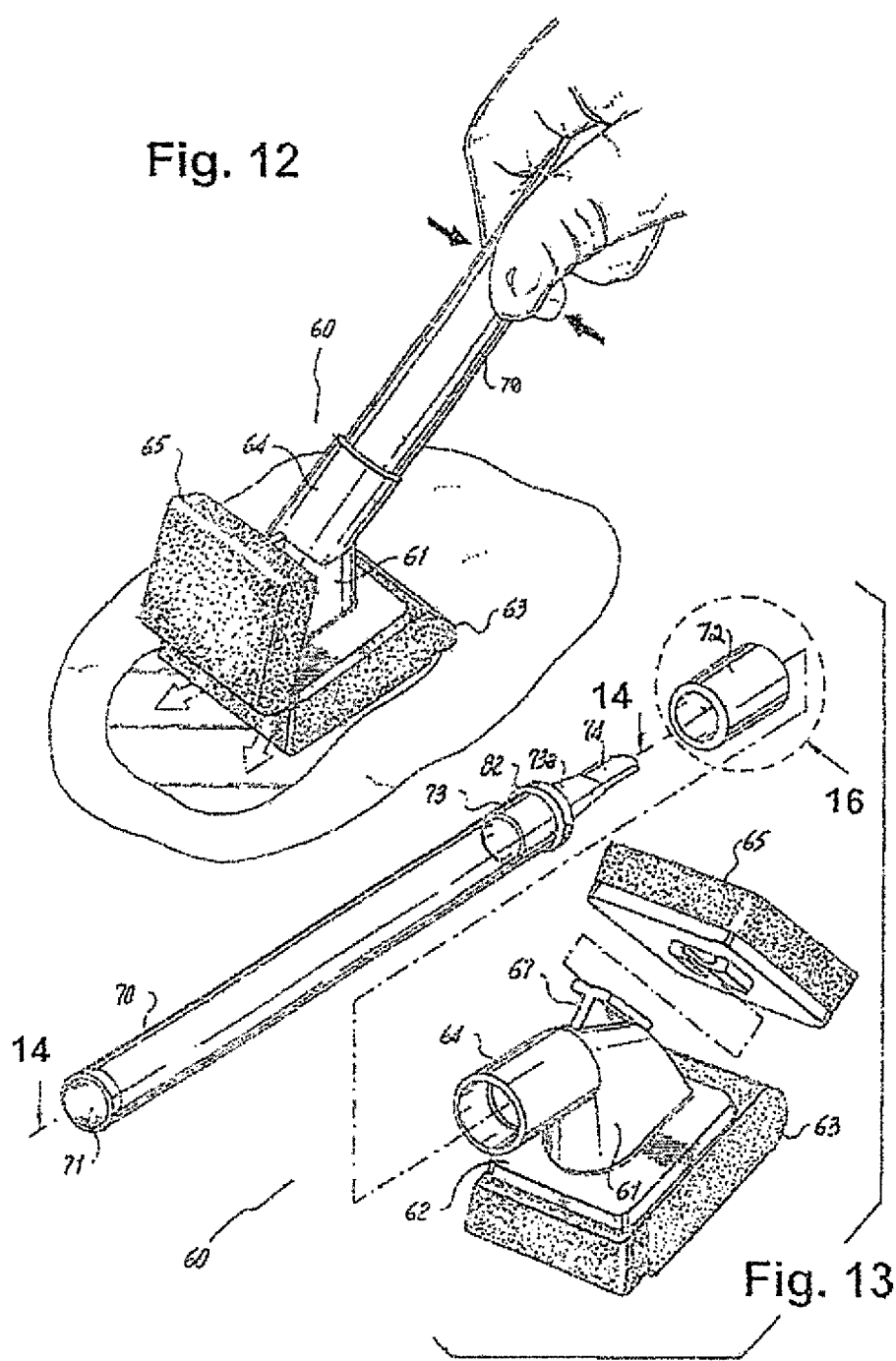

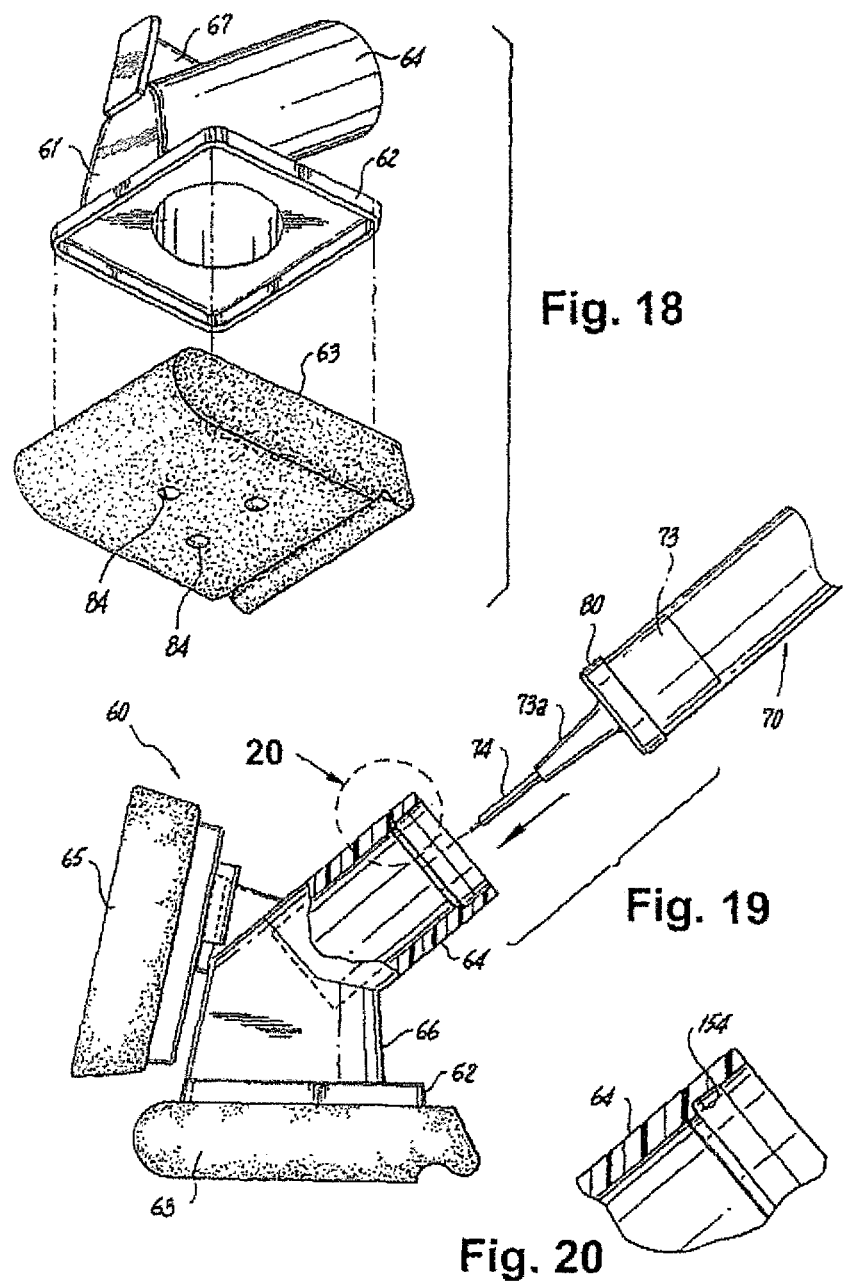

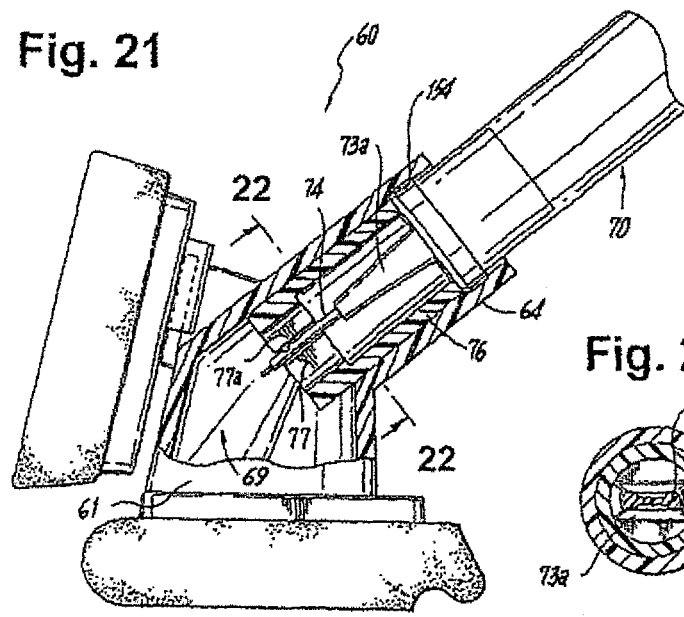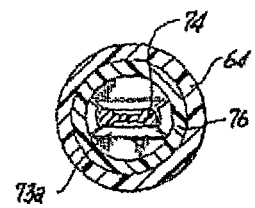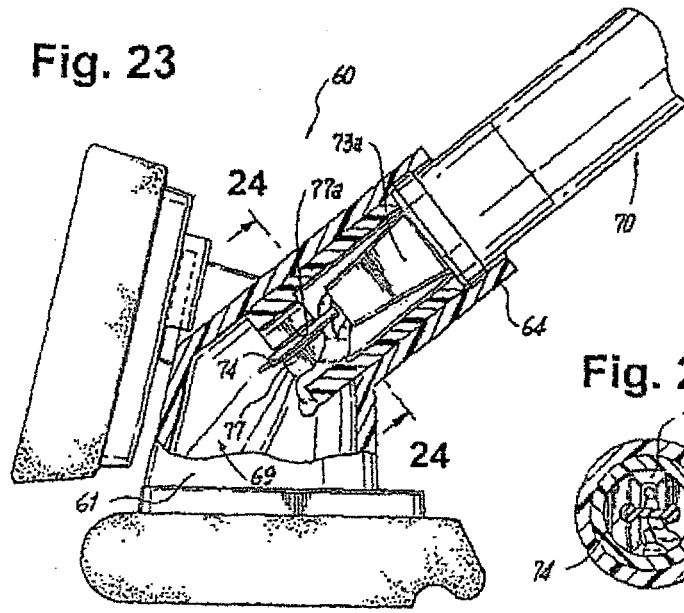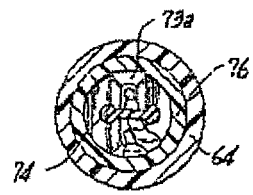

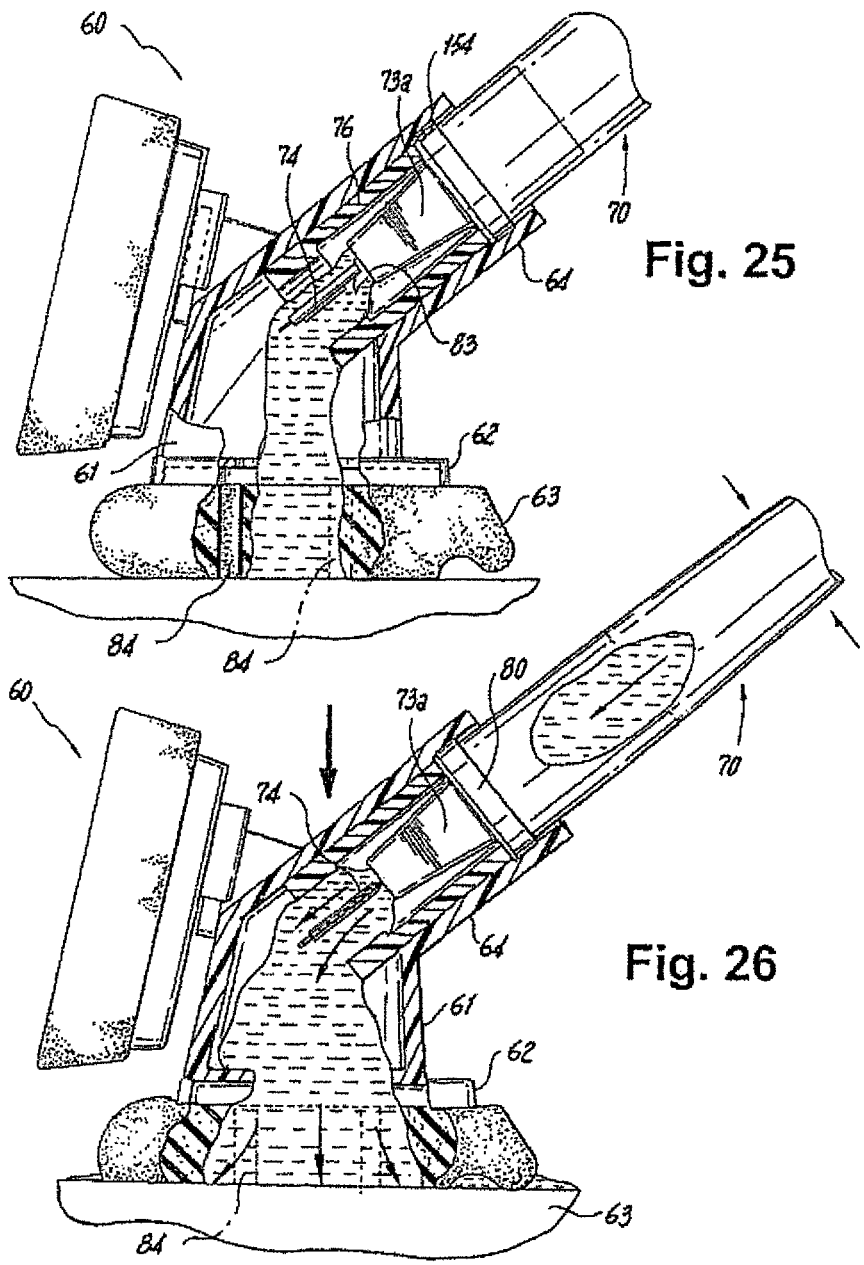

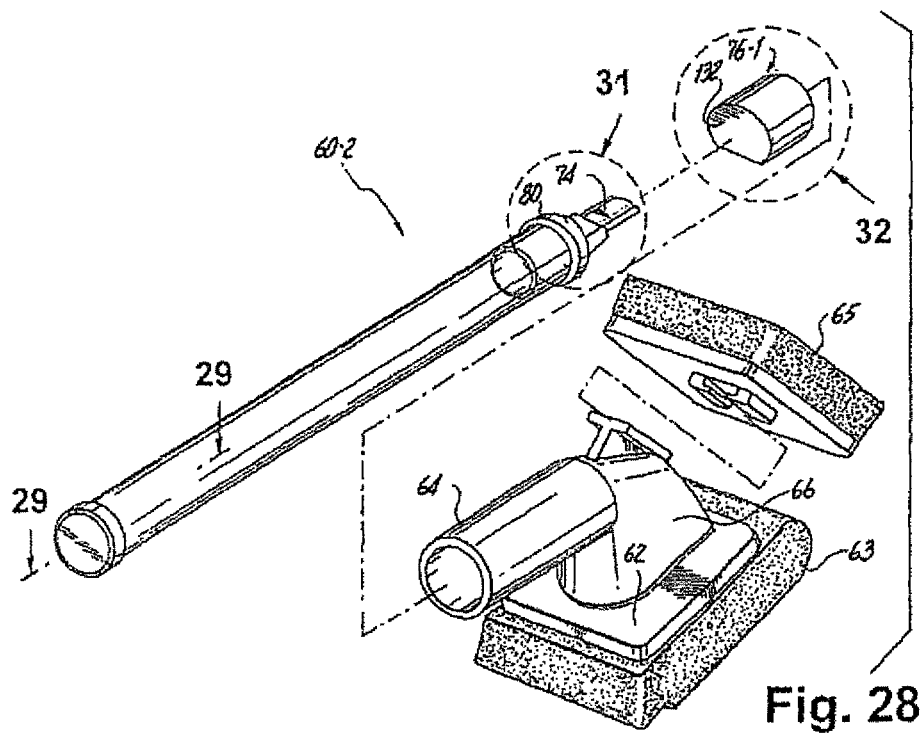
Fig. 28
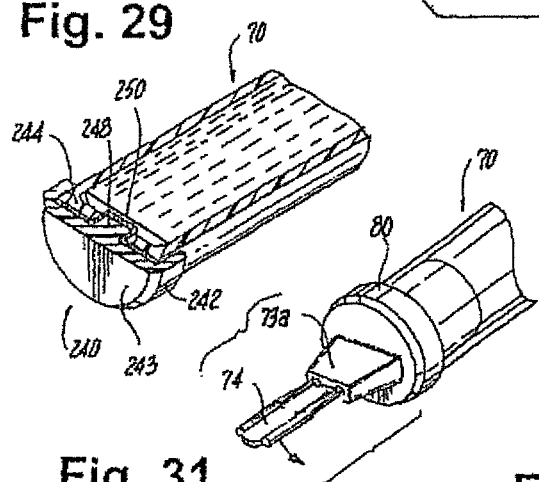
Fig. 29
Fig. 31
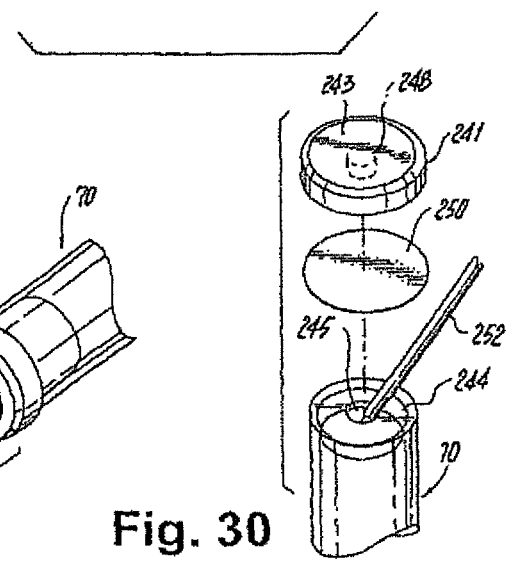
Fig. 30

DISPENSING APPLICATOR FOR FLUIDS

CROSS REFERENCE TO RELATED APPLICATIONS

This application is a continuation application of, and claims priority from, U.S. application Ser. No. 13/306,681 filed Nov. 29, 2011 (now allowed), which is a continuation of U.S. application Ser. No. 11/740,910 filed Apr. 26, 2007, now U.S. Pat. No. 8,083,425 issued Dec. 27, 2011, which is a continuation-in-part of U.S. application Ser. No. 11/138,142 filed May 26, 2005, now U.S. Pat. No. 7,614,811 issued Nov. 10, 2009.

FIELD OF THE INVENTION

The present invention is directed in general to means for swabbing a surface (i.e., skin) that is gripped by a user at one end and has a sponge or absorbent material at the other end. Further, the present invention is directed to such means for swabbing a surface having a source of a fluid (e.g., disinfectant or medicament) in communication with the sponge or absorbent material. Specifically, the present invention is directed to such a fluid-containing means for swabbing a surface further having means that is fractured or separated for the purpose of allowing the fluid to flow from the fluid source to the sponge or absorbent material.

BACKGROUND OF THE INVENTION

Applicators consisting of a wooden or plastic tube having a bud of cotton on one or both ends, are widely used for numerous purposes, such as the topical application of substances to the human body. A demand exists for a product of this kind, which serves not only as an applicator, but also as a container for substances that are to be applied to the human body. To be practical, such a device would have to have a manually frangible portion that can readily be broken, while at the same time being so constructed so as to prevent inadvertent fracture. An applicator of this nature would be useful for numerous purposes.

Prior dispensing applicators allow excess amount fluid to flow too quickly, and the fluid tends to pool on the surface. Depending upon the fluid being dispensed, such pooling can lead to patient discomfort, chemical burns, and even electrical shock if the dispensed fluid comes into contact with electrical leads attached to the patient's body.

Moreover, in prior art dispensing applicators, the dispensed fluid tends to accumulate at the rear-most portion of the absorbent member, which is closest to the fluid source, instead of preferably evenly spreading throughout the absorbent member. As the volume of the dispensed fluid gradually increases at the rear portion of the absorbent member, the fluid starts uncontrollably dripping, thus, causing substantial inconvenience to a user.

A need, therefore, exists for a dispensing applicator overcoming the above-identified drawbacks of the known related art.

A further need exists for a hand-held dispensing applicator that has a simple structure allowing the practitioner to deliver fluid to the surfaces to be treated in a controllable manner.

Another need exists for a dispensing applicator that has an easily actuatable structure requiring minimal application of manual force.

Further, a need exists for a hand-held dispensing applicator that has a structure minimizing uncontrollable distribution of fluid.

SUMMARY OF THE INVENTION

In light of the foregoing, the present invention provides a hand-held dispensing applicator comprising a source of fluid, a frangible applicator tip attached to the fluid source, and an absorbent member attached to the frangible applicator tip. When the frangible applicator tip is broken, fluid flows from the source to the absorbent member, whereby the fluid is applied and spread on a surface. Preferably, the fluid is applied and spread on a surface in a controlled amount. Preferably, the fluid source is in the shape of a hollow tube container that is integrally formed, as a single piece, from a relatively rigid synthetic resinous material. Preferably, the frangible applicator tip comprises a support element permanently connected to the fluid source, a relatively rigid tongue element extending outwardly of the support element at an end of the container, and a frangible region therebetween. Extending through the support element is a fluid conduit that is open at the end attached to the fluid source and sealed by the tongue element at the end attached to the absorbent member. By deflecting the tongue element relative to the support element, with a force of substantially predetermined magnitude, the frangible region between the tongue and support elements will fracture, thereby permitting fluid to flow from the fluid source through the conduit, and into the attached absorbent member. Preferably, the tongue element comprises ribs for reinforcing the tongue element to resist unintentional breaking of the frangible region. More preferably, the applicator tip comprises a semi-permeable or non-permeable cover disposed around the frangible region to control the speed and direction of the dispersion of the fluid in the absorbent member.

In another embodiment, the dispensing applicator comprises a mounting body which has a stem piece extending from a mounting body top part, and a lower body part which carries at an underside of the latter, an absorbent applicator. An elongated fluid container having a first end is attachable at a second opposite end thereof and with a snap fit, in the stem piece. The container includes a frangible region remote from said first end, and a rigid tongue element extends longitudinally from the frangible region, a tip end of the tongue element defining the container opposite second end.

A fracture anvil is disposed in the stem piece. To fracture the container frangible region to release fluid there from to the absorbent applicator, a relative movement between the container, i.e., the tongue element thereof and the fracture anvil is effected. This is done with the tongue element in contact with the fracture anvil. The contact and relative movement produce the rupture of the frangible region and, more specifically at the joinder location of the tongue element and frangible region.

In one form, the fracture anvil is a cylindrical body having a cruciform passage extending therethrough and which receives the flat blade-like tongue element. By effecting a relative rotation between the fracture anvil and the container, the fracture of the frangible region results.

In another form, the fracture anvil is a truncated cylinder received in the stem piece. By urging the container axially into the stem piece and against an inclined end face of the fracture anvil, the tongue element is deflected laterally from its normal disposition to cause the rupture at the joinder location thereof with the remainder frangible region. With the joinder structure ruptured, the fluid contents release from the container. Flow gutters or channels are defined in the fracture anvil to insure free contents flow from the container past or through the fracture anvil to the absorbent applicator. The arrangement of the tongue element and its structure is designed such as to allow retention of at least one ribbon residue material connecting the tongue element to the frangible region precluding passing of the tongue element into a contents flow channel wherein it could impede or block flow to the absorbent applicator.

A further feature provides a snap fit cap fitted on an opposite contents filling end of the container opposite the tongue member end, and provided with a seal that excludes any possible and contaminating air presence in the contents at said container end.

Other objects, features and advantages of the present invention will be apparent from the following detailed description taken in connection with the accompanying drawings.

BRIEF DESCRIPTION OF THE DRAWINGS

FIG. 5B is a diagrammatic view illustrating two positions of the dispensing applicator of FIG. 5;

FIG. 11A is a side cross-sectional view of another dispensing applicator according to the present invention;

FIG. 11B is a side cross-sectional view of a further aspect of an embodiment of the dispensing applicator according to the present invention.

FIG. 12 is a left front side perspective view of another embodiment of dispensing applicator wherein a fluid containing source is receivably attachable to an applicator mounting body stem piece in snap fit connection therewith, initiation of fluid flow being effected with a relative rotative movement between the fluid source container and a fracture anvil in the mounting body;

FIG. 13 is a right side exploded view of the FIG. 12 dispensing applicator;

FIG. 18 is an exploded left front side perspective of the mounting block which receives an absorbent applicator at a block bottom side;

FIG. 19 is a left side elevation view partly in section of the mounting block, the absorbent applicator being affixed at the block bottom side, and an absorbent swab member being affixed to a block front side adjacent to said bottom side, the fluid source container being depicted in position just before the tongue carrying end thereof is inserted into the mounting block;

FIG. 20 is a fragmentary section view of an upper inlet part of the mounting block stem piece indicated in the circle 20 portion in FIG. 19, there being an annular slot inside adjacent entry to the upper inlet, said slot defining a detent for retaining a flange on the container to effect snap fit of the container to the applicator mounting body.

FIG. 21 is a left side elevation view similar to FIG. 19 showing the fracture anvil received in the mounting block with the tongue element positioned in the cruciform passage in pre-fracture condition, the container being snap fitted to the mounting block;

FIG. 22 is a section view taken on the line 22-22 in FIG. 21;

FIG. 23 is a view similar to FIG. 21 but showing the post fracture position of the fracture anvil, which has been rotated approximately ninety degrees from the position it occupied in FIG. 21;

FIG. 24 is a section view taken on the line 24-24 in FIG. 23;

FIG. 25 is a view similar to FIG. 23 except it is more broken away to depict how on occurrence of fracture of the frangible piece, fluid starts to flow from the apertures at the fracture point and disperses through the absorbent applicator;

FIG. 26 is a view similar to FIG. 25 but showing a more profuse flow of fluid occurring following fracturing of the frangible piece;

FIG. 28 is a right side exploded perspective view of another embodiment of dispenser employing a fracture anvil for fracturing the tongue element at its joinder point with the frangible length thereby to initiate release of the container contents into the absorbent applicator;

FIG. 29 is a fragmentary length portion of the container in half section taken on line 29-29 in FIG. 28 depicting the manner of the capping of the container contents filling end;

FIG. 30 is an exploded fragmentary perspective view of several components embodied in the capped end structure of the container;

FIG. 31 is a fragmentary perspective view of the applicator tongue element carrying end in circle portion 31 of FIG. 28, depicting the tongue element as fractured separated from the frangible section solely for the purpose of illustrating the apertures from which container fluid contents issue therefrom into the absorbent applicator, it being understood that in the embodiment where the tongue element is fractured with urging against a fracture anvil, it is preferable that the tongue element on fracturing, have retained structure by which it remains attached to the frangible length while still allowing meaningful fluid contents flow;

DETAILED DESCRIPTION OF THE PREFERRED EMBODIMENTS

Figure 1:
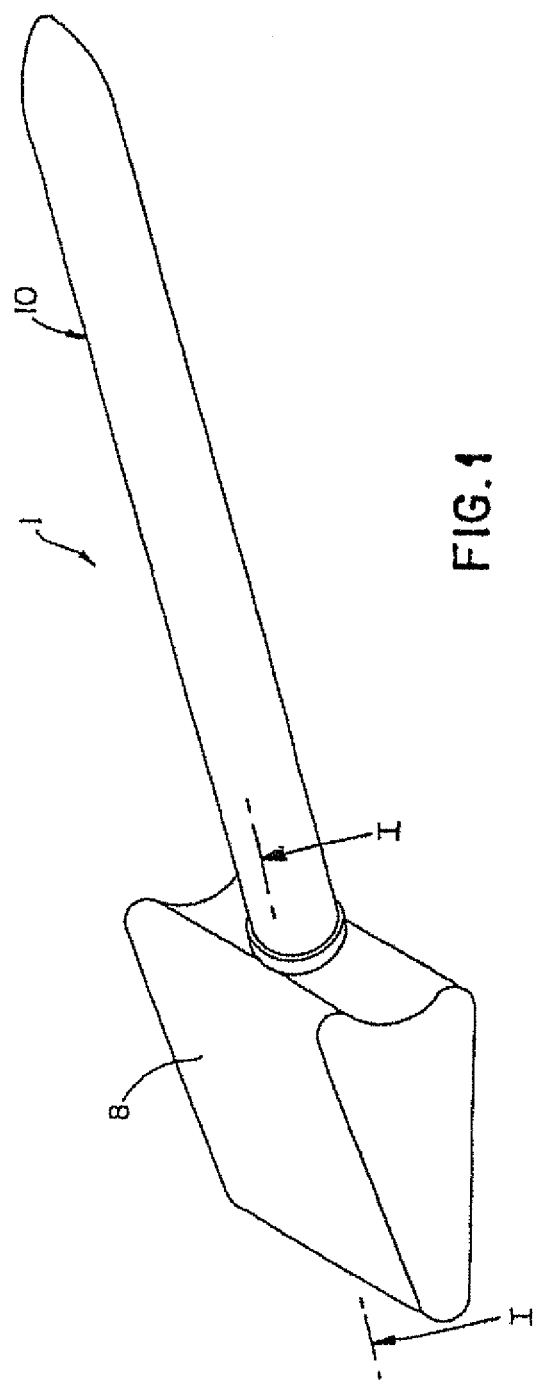
FIG. 1 is a side elevation view of a dispensing applicator according to the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

Figure 2:
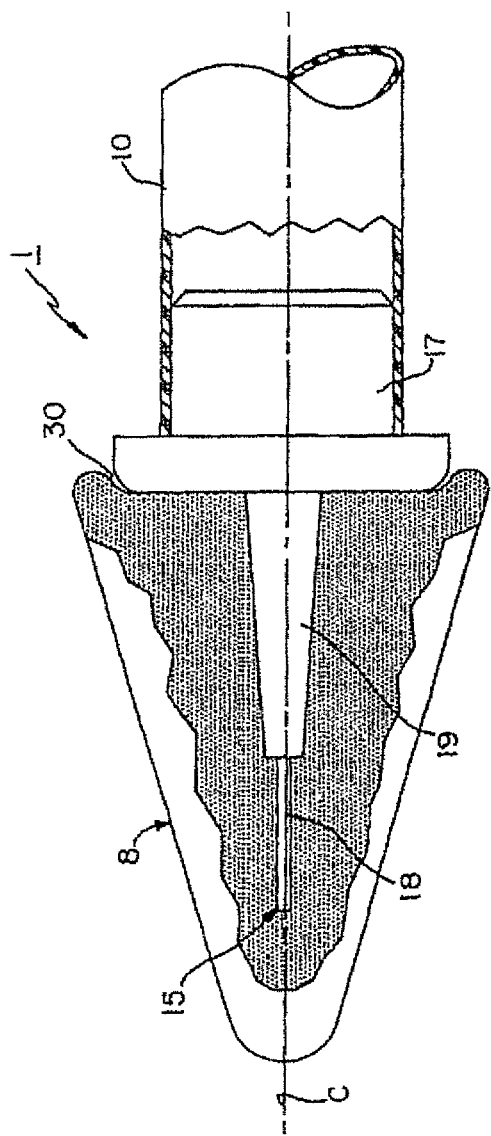
FIG. 2 is a side cross-sectional view of the dispensing applicator of FIG. 1.

Referring now to the drawings, FIGS. 1 and 2 in particular, illustrate a dispensing applicator according to the present invention generally indicated as reference numeral 1. Dispensing applicator 1 comprises an absorbent applicator member 8, a fluid source 10, and an applicator tip 15. Absorbent member 8 may be of any suitable shape, such as cubic, cylindrical, or conical, and comprise any suitable absorbent material, such as cotton or sponge. Fluid source 10 may have any suitable shape. As shown in FIG. 1, fluid source 10 is preferably a hollow, generally cylindrical body. The end of fluid source body located adjacent to absorbent member 8 is preferably sealed thereto at a joint or seam 30, such as by heat sealing, to enclose the fluid substance contained within fluid source body 10. Applicator tip 15 comprises an attachment member 17 and tongue member 18 joined thereto by a tapered frangible region or juncture 19.

Tongue member 18 is preferably a flat and broad shape that extends a distance into absorbent member 8, such that tongue member 18 is longer than it is wide (see FIGS. 4A to 4D). It should be noted that the attachment member 17 is relatively thick adjacent the fluid source body 10, and tapers toward frangible juncture 19. Absorbent member 8 is preferably connected to attachment member 17 and/or fluid source body 10.

The manner of utilizing dispensing applicator 1 will be self-evident, and simply involves holding the dispensing applicator 1 with the absorbent application member 8 against an application surface. Dispensing applicator 1 is held such that tongue member 18 is at an acute angle (i.e., substantially parallel) to the application surface. Sufficient downward pressure of tongue member 18 against the application surface will deflect tongue member 18 from the central axis c of the fluid source body 10. At a predetermined amount of deflection, the frangible juncture 19 will fracture or break proximate the intersection thereof but will not separate. Fracture of the frangible juncture 19 will desirably be achieved by the application of approximately 0.25 to 5 pounds of force of tongue member 18 against the application surface and will cause opening for fluid flow proximate junctures or apertures 12 as will be discussed more fully below.

Figure 3B:
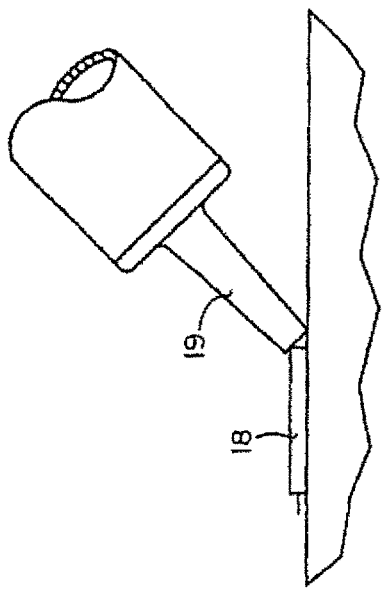
FIG. 3B is a side elevation view of the applicator tip of FIG. 3 wherein the frangible region is broken.
Figure 3C:
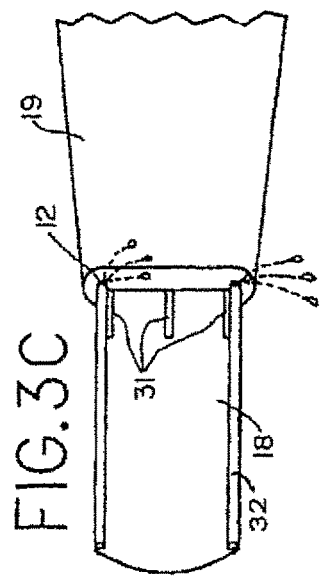
FIG. 3C is a top view of the applicator tip of FIG. 3B wherein apertures are formed in the broken frangible region.

As shown in FIGS. 3B and 3C, breaking frangible juncture 19 will result in the formation of one or more apertures 12 through which fluid from source body 10 may flow into absorbent member 8 (not shown), but fluid flow is shown from apertures 12, such that tongue portion 18 remains flexibly fixed to frangible juncture member 19 and is prohibited from separation. In other words, fracture of the region proximate apertures is required, but tongue portion 18 remains flexibly joined along a hinge line and is strengthened by rib members 31, as will be discussed.

In its most preferable form, all portions of the source body 10 will have a wall thickness that is substantially uniform at a value of about 0.005 inch to about 0.025 inch (about 0.127 mm to about 0.635 mm), but may become thinner proximate regions 12 to urge ready fracture. The source body 10 is preferably made of polypropylene having a density of 0.897 g/cm$^2$ and a flexural modulus of about 150 Kpsi (about 1035 MPa), as determined by ASTM method 79013. The source body 10 is preferably about 6 inches to about 10 inches in overall length, and about 0.25 to about 1.0 inches in diameter, so as to be convenient to grasp and still contain sufficient fluid for a single application.

The applicator tip 15 is about 1 to 3 inches long, and about 0.325 inches in diameter. The frangible juncture 19 will preferably have a thickness of about 0.0005 inch to about 0.002 inch (about 0.013 mm to about 0.050 mm). The one or more apertures 12, which are produced by the fracture of frangible juncture 19, but not the separation of tongue member 18, may be of any suitable size, but preferably have a width and height that is substantially correlated to the width and thickness of large ribs 31, 32 (see FIG. 3).

Figure 3A:
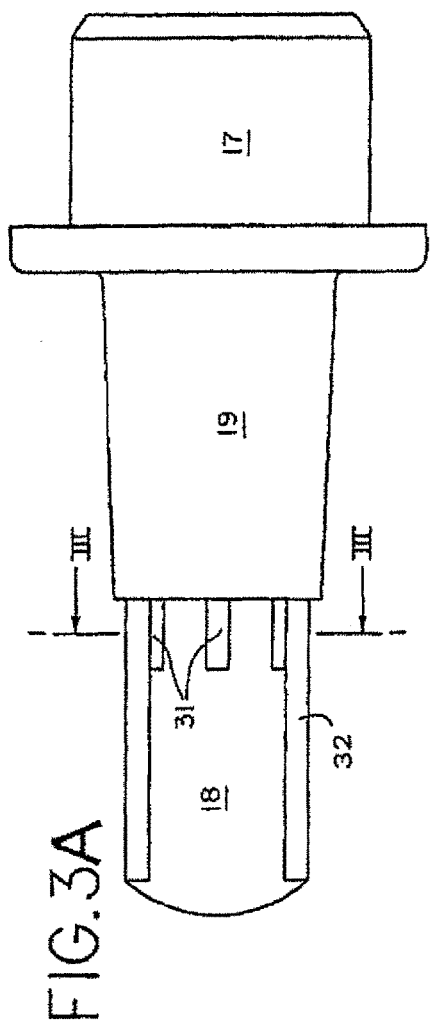
FIG. 3A is a front elevation view of a preferred applicator tip for the dispensing applicator of FIG. 1.

Referring to FIGS. 3A and 3C, tongue member 18 preferably comprises a plurality of reinforcing ribs 31, 32. Due to the reinforcing ribs and the resultant rigidity of tongue member 18, there will be reduced flex along the length of tongue 18, and an applied force on tongue member 18 will be effectively entirely transferred to and concentrated at frangible juncture 19 proximate apertures 12. The result will be the reliable fracturing of frangible juncture 19 proximate apertures 12, which fracturing results in the formation of one or more apertures 12 of suitable size on the same side as the force application to permit the fluid within the fluid source body 10 to be discharged therefrom and distributed across a predetermined area of absorbent application member 8 (FIG. 1). As noted above, it will generally be desirable for the material forming fluid source body 10 to be sufficiently thin to permit some compression of fluid source body 10, so as to enable discharge of a liquid therein at a faster rate than would otherwise occur, and/or to promote the flow of the fluid, especially if the fluid is relatively viscous. While in a first use apertures 12 may only fracture along a portion of the aperture directing fluid flow along one side (the force application side) if force is directed in the opposite direction, apertures 12 will fracture along their remaining region, retaining tongue member 18 only by the flexible hinge between apertures 12 and strengthening ribs 31.

Figures 4A, 4B:
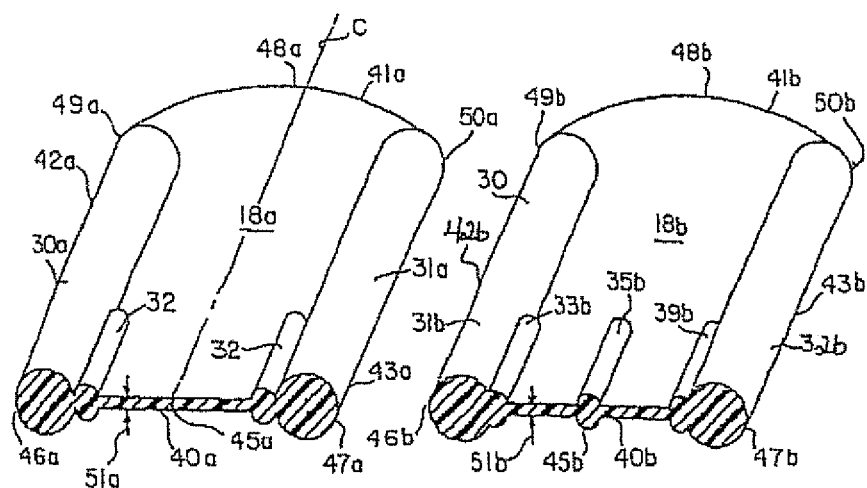
FIG. 4A is a perspective view of a first preferred tongue member for an applicator tip for the dispensing applicator of FIG. 1.
FIG. 4B is a perspective view of a second preferred tongue member for an applicator tip for the dispensing applicator of FIG. 1.

FIG. 4A illustrates a first arrangement of ribs for a tongue 18a. As shown, tongue 18a is rectilinear in shape with a bottom edge 40a, a top edge 41a, and side edges 42a, 43a. Bottom edge 40a is substantially linear with a central point 45a and corners 46a, 47a at which the proximate ends of respective side edge 42a, 43a meet. Top edge 41a is curvilinear with an apex 48a and corners 49a, 50a at which the distal ends of respect side edges 42a, 43a terminate. Central point 45a and apex 48a lie along central axis c. The distance between central point 45a and apex 48a is the length of tongue 18a, while the distance between corners 49a, 50a is the width of tongue 18a. The thickness 51a of tongue 18a is the distance between the top and bottom surfaces thereof. Side edges 42a, 43a each have a respective large rib 31a, 30a extending along the entire length thereof. It is notable that tongue 18a extends a distance beyond the length of the large ribs 31a, 30a to apex 48a, whereby top edge 41a is not reinforced. Ribs 31a, 30a are each about 3 times the thickness of tongue 18a and about $\frac{1}{5}^{th}$ the width of tongue 18a. Small ribs 32 are disposed directly adjacent to their respective large rib 31a, 30a on the side thereof that is proximate to central axis c. Each small rib 32 extends from bottom edge 40a for a distance that is about $\frac{3}{10}^{th}$ the length of the large ribs 31a, 32a. Each small rib 32 is about 2 times the thickness of tongue 18a and about $\frac{1}{10}^{th}$ the width of tongue 18a.

FIG. 4B illustrates a second arrangement of ribs for a tongue 18b. As shown, tongue 18b is rectilinear in shape with a bottom edge 40b, a top edge 41b, and side edges 42b, 43b. Bottom edge 40b is substantially linear with a central point 45b and corners 46b, 47b at which the proximate ends of respective side edge 42b, 43b meet. Top edge 41b is curvilinear with an apex 48b and corners 49b, 50b at which the distal ends of respect side edges 42b, 43b terminate. Central point 45b and apex 48b lie along central axis c (see FIG. 2). The distance between central point 45b and apex 48b is the length of tongue 18b, while the distance between corners 49b, 50b is the width of tongue 18b. The thickness 51b of tongue 18b is the distance between the top and bottom surfaces thereof. Side edges 42b, 43b each has a respective large rib 31b, 32b extending along the entire length thereof. Large ribs 31b are each about 3 times the thickness of tongue 18b and about $\frac{1}{5}^{th}$ the width of tongue 18b. Small half-ribs 33b, 34b are disposed directly adjacent to their respective large ribs 31b on the sides thereof that are proximate to central axis c. A small rib 35b is disposed along central axis c. Each small half-rib 33b, 34b extends from bottom edge 40b a distance that is about $\frac{3}{10}$ the length of the large ribs 31b. Each small half-rib 33b, 34b is about 2 times the thickness of tongue 18b and about $\frac{1}{20}^{th}$ the width of tongue 18b. The small rib 35b extends from bottom edge 40b a distance that is about $\frac{3}{10}$ the length of the large ribs 31b. The small rib 35b is about 2 times the thickness of tongue 18b and about $\frac{1}{10}^{th}$ the width of tongue 18b.

Figures 4C, 4D:
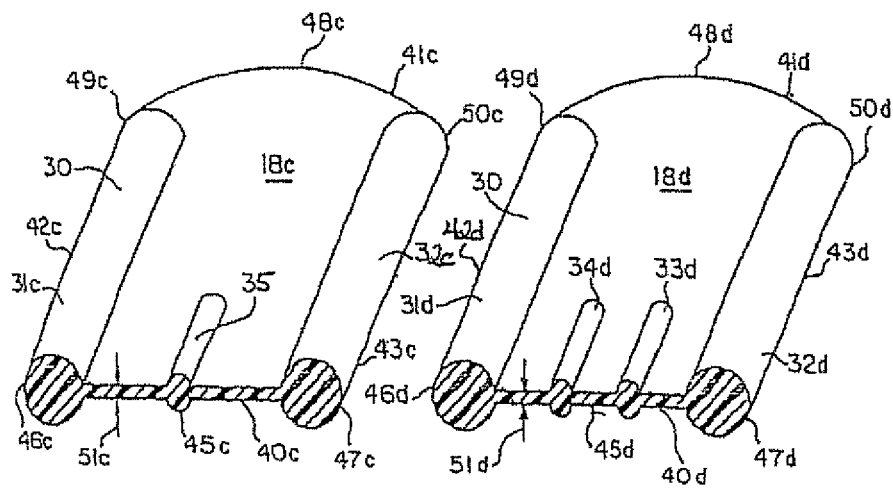
FIG. 4C is a perspective view of a third preferred tongue member for an applicator tip for the dispensing applicator of FIG. 1.
FIG. 4D is a perspective view of a fourth preferred tongue member for an applicator tip for the dispensing applicator of FIG. 1.

FIG. 4C illustrates a third arrangement of ribs for a tongue 18c. As shown, tongue 18c is rectilinear in shape with a bottom edge 40c, a top edge 41e, and side edges 42c, 43c. Bottom edge 40c is substantially linear with a central point 45c and corners 46c, 47c at which the proximate ends of respective side edge 42c, 43c meet. Top edge 41c is curvilinear with an apex 48c and corners 49c, 50c at which the distal ends of respect side edges 42c, 43c terminate. Central point 45c and apex 48c lie along central axis c (see FIG. 2). The distance between central point 45c and apex 48c is the length of tongue 18c, while the distance between corners 49c, 50c is the width of tongue 18c. The thickness 51c of tongue 18c is the distance between the top and bottom surfaces thereof. Side edges 42c, 43c each has a respective large rib 31c, 32e extending along the entire length thereof. Large ribs 31c, 32c are each about 3 times the thickness of tongue 18c and about $\frac{1}{5}^{th}$ the width of tongue 18c. A small rib 35e is disposed along central axis c. The small rib 35c extends from bottom edge 40c a distance that is about $\frac{3}{10}$ the length of the large ribs 31. The small rib 35c is about 2 times the thickness of tongue 18c and about $\frac{1}{10}^{th}$ the width of tongue 18c.

FIG. 4D illustrates a fourth arrangement of ribs for a tongue 18d. As shown, tongue 18d is rectilinear in shape with a bottom edge 40d, a top edge 41d, and side edges 42d, 43d. Bottom edge 40d is substantially linear with a central point 45d and corners 46d, 47d at which the proximate ends of respective side edge 42d, 43d meet. Top edge 41d is curvilinear with an apex 48d and corners 49d, 50d at which the distal ends of respect side edges 42d, 43d terminate. Central point 45d and apex 48d both lie along central axis c (see FIG. 2). The distance between central point 45d and apex 48d is the length of tongue 18d, while the distance between corners 49d, 50d is the width of tongue 18d. The thickness 51d of tongue 18d is the distance between the top and bottom surfaces thereof. Side edges 42d, 43d each has a respective large rib 31d, 32d extending along the entire length thereof. Large ribs 31d, 32d are each about 3 times the thickness of tongue 18d and about $\frac{1}{5}^{th}$ the width of tongue 18d. Spaced apart from each large rib 31d, 32d is a respective small rib 33d, 34d. The small ribs 33d, 34d are spaced apart from each other and evenly spaced from central axis c. The small ribs 33d, 34d are closer to central axis c than to their respective large ribs 31d, 32d. The small ribs 33d, 34d extend from bottom edge 40b a distance that is about $\frac{3}{10}$ the length of the large ribs 31d, 32d. The small ribs 33d, 34d are about 2 times the thickness of tongue 18b and about 1/10th the width of tongue 18b. Each small rib 33d, 34d is spaced apart from the central axis c by a distance that is approximately equal to its respective width. The small ribs 33d, 34d are spaced apart from each other by a distance that is approximately equal to 2 times the width of either small rib 33d or 34d. Each small rib 33d, 34d is spaced apart from its respective large rib 31d, 32d by a distance that is approximately equal to 2 times its respective width.

Figure 5A:
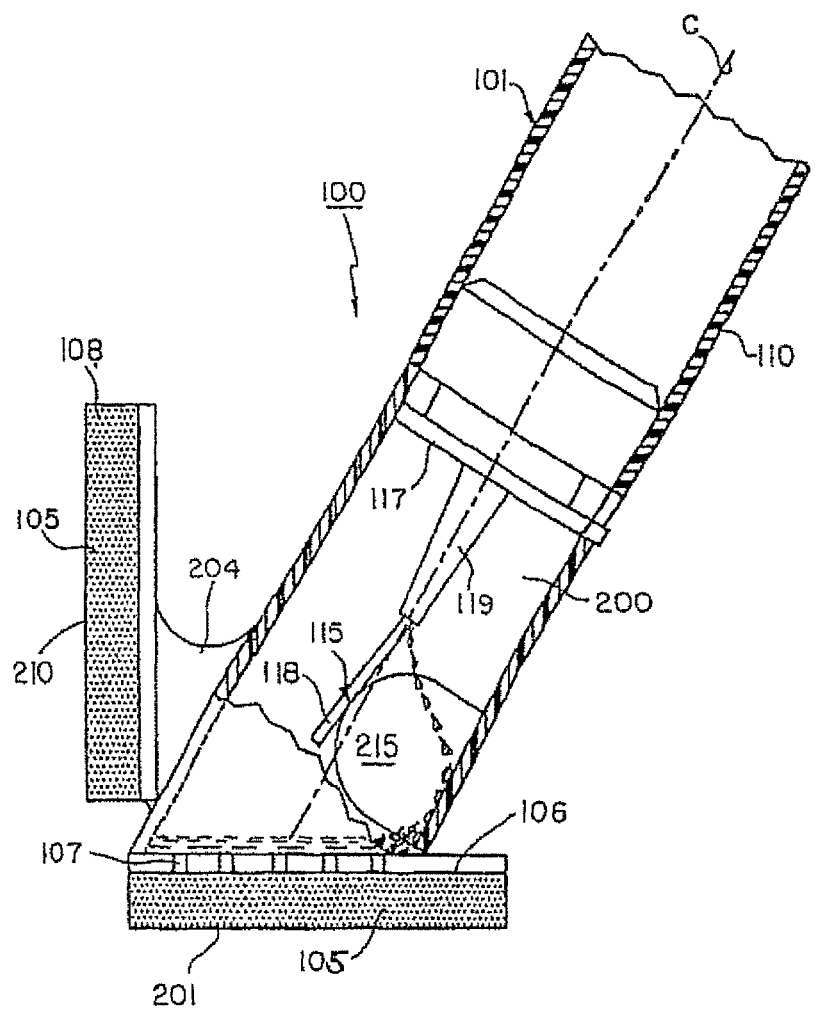
FIG. 5A is a cross-sectional side view of the dispensing applicator constructed in accordance with a further embodiment of the invention.

FIGS. 5A and 5B illustrate a second dispensing applicator 100 according to the present invention. Dispensing applicator 100 comprises an applicator head 108, a source of fluid, which is shown as a hollow, generally cylindrical body 110, and an applicator tip 115, which has an attachment member 117 and tongue member 118 joined thereto by a tapered frangible juncture member 119 having fracture sites as noted above at 12. Fluid source body 110 and applicator tip 115 are respectively identical in form and function to fluid source body 10 and applicator tip 15 described hereinabove in reference to FIGS. 1 through 4D.

In addition, dispensing applicator member 100 is provided with an absorbent swab member 201, and an inwardly projecting ridge-shaped member 215 provided within body 110. A portion of body 110 is adapted to hold and/or support absorbent applicator member 105. As shown, absorbent applicator member 105 is held and supported on a surface 106. Surface 106 is provided with at least one aperture 107, such that the fluid may flow from the interior of body 110 into absorbent applicator member 105, as discussed in further detail herein below. Furthermore, a portion of body 110 is adapted to hold and/or support absorbent swab member 210.

As shown, absorbent swab member 210 is held and supported on a surface 203 that is connected to body 110 by a stock member 204. Absorbent swab member 210 is preferably not in fluid communication with the interior of body 110. Outer surface 201 of absorbent applicator member 105 is oriented relative to body 200 such that, when absorbent applicator member 105 is substantially parallel to an application surface (i.e., in contact with the application surface), the central axis c of body 110 forms an angle of about 45° with the application surface, which angle provides a comfortable grip for the user and facilitates the flow of fluid through the interior of body 110 into absorbent application member 105. Similarly, absorbent applicator member 105 of absorbent swab member 210 is oriented relative to body 200, such that, when absorbent swab member 210 is substantially parallel to an application surface (i.e., in contact with the application surface), the central axis c of body 200 forms an angle of about 30° with the application surface, which angle provides a comfortable grip for the user and allows the user to spread the applied fluid over a relatively large area with relatively less arm movement and/or extension.

The manner of utilizing dispensing applicator 100 involves holding the dispensing applicator 100 with the absorbent application member 105 against an application surface. Downward pressure of applicator 100 against the application surface will displace head 108 upwardly and force ridge-shaped member 215 into contact with tongue member 118. Sufficient upward pressure of ridge-shaped member 215 against tongue member 118 will upwardly deflect the tongue member 118 from the central axis c of the fluid source body 110. At a predetermined amount of deflection, the frangible juncture 119 will fracture or break at apertures 12 (not shown), but not along the entire hinge region or at strengthening ribs (not shown) preventing unintended separation. Fracture of the frangible juncture 119 will desirably be achieved by the application of approximately 0.25 to 5 pounds of downward force of applicator 100 against the application surface. Breaking frangible juncture 119 will result fluid from fluid source body 110 flowing into head 108 via apertures 12 (not shown, but noted in FIGS. 3A-3C). Comparable to breaking frangible region 19 of applicator tip 15, as discussed herein above in reference to FIGS. 3A to 3C, breaking frangible region 119 of applicator tip 115 results in the formation of one or more apertures in applicator tip 115 through which fluid from source body 110 may flow into head 108 without the unintended separation of the tip member 115. Thus, in general, applicator tip 15 is comparable in form and structure to applicator tip 115.

Absorbent swab member 210 may be employed for a variety of purposes. Swab 210 may be used to spread a fluid over the application surface after the application member 205 initially applies the fluid. Using swab 210 in this way would be particularly advantageous if the amount of fluid that is desired to cover a relatively large surface area has been inadvertently applied to a relatively small area, which may occur if application member 105 becomes over-saturated with fluid and can no longer effectively regulate the flow rate and amount of fluid being applied. Moreover, swab member 210 may be used to soak up fluid on the application surface, for example, when an excess of fluid has been applied or the fluid has been applied over the wrong area.

As stated above, absorbent swab member 210 is preferably not in fluid communication with the interior of body 200. However, a possible use for swab 210 is applying fluid to a second surface area that is separate and apart from the surface area over which used absorbent application member 205. In the critical interest of avoiding cross-contamination, it is desirable to use the application member 105 over only a single contiguous surface area that should be relatively limited (e.g., the upper front of the torso, instead of the entire front of the torso). Accordingly, after an initial application, any additional fluid in a given dispensing applicator may go wastefully unutilized. Therefore, in another embodiment of absorbent applicator head 108, there is provided at least one aperture (not shown) in surface 203, such that fluid may fluid from the interior of body 200 into absorbent swab member 210.

Head 108 may be detachable from fluid body 110. Fluid body 110 may contain an amount of fluid that is greater than is necessary for a given application. Accordingly, after an initial application, any additional fluid in a given dispensing applicator may go wastefully unutilized. Therefore, in another embodiment of applicator 100, fluid body 110 is removably attached to head 108 so that head 108 may be disposed of separately from fluid body 110. If fluid body 110 contains residual fluid after an initial application, other absorbent head may be attached to fluid body 110, thereby allowing the residual fluid to be applied to another application surface.

Figure 6:
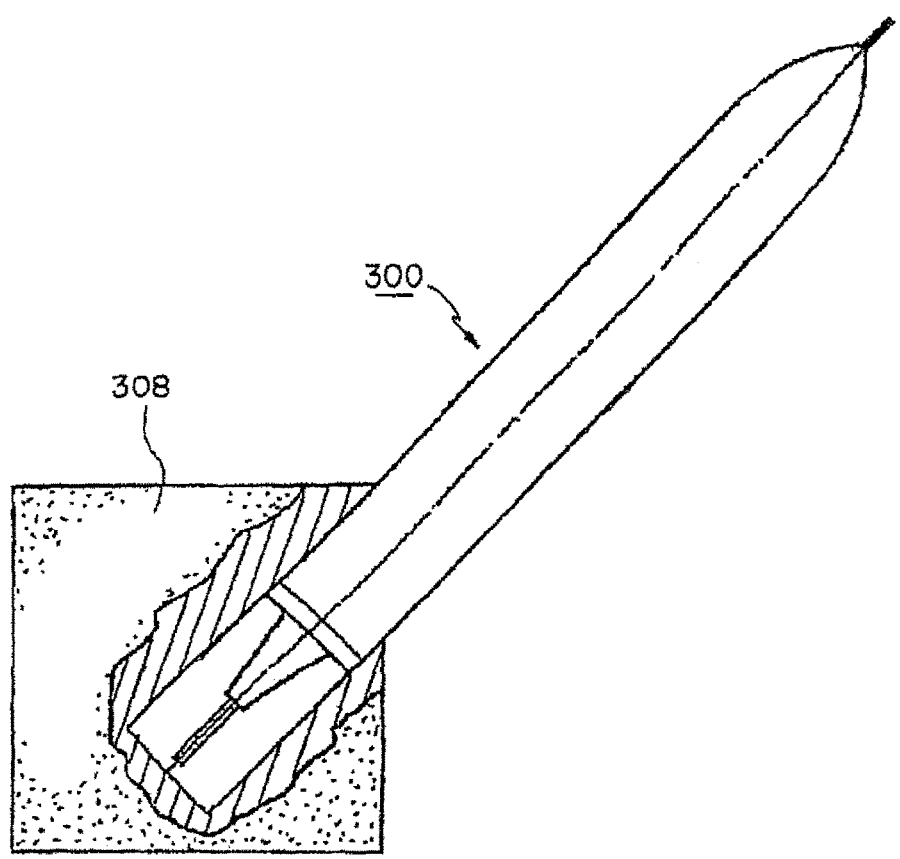
FIG. 6 is a side view of a dispensing applicator structured in accordance with a further embodiment of the present invention and showing a cross-sectional side view of the applicator tip.

Referring to FIG. 6, as stated above, it is desirous to avoid cross-contamination by using a given absorbent applicator over only a single contiguous, relatively limited, surface area. Yet, using a given absorbent application in such a manner will often result in an amount of fluid therein being wasted. Accordingly, a dispensing applicator according to the present invention, generally indicated as reference numeral 300, may be provided with a relatively larger, multi-sided absorbent applicator member 308, such that different sides thereof may be used on different surface areas.

Figure 7:
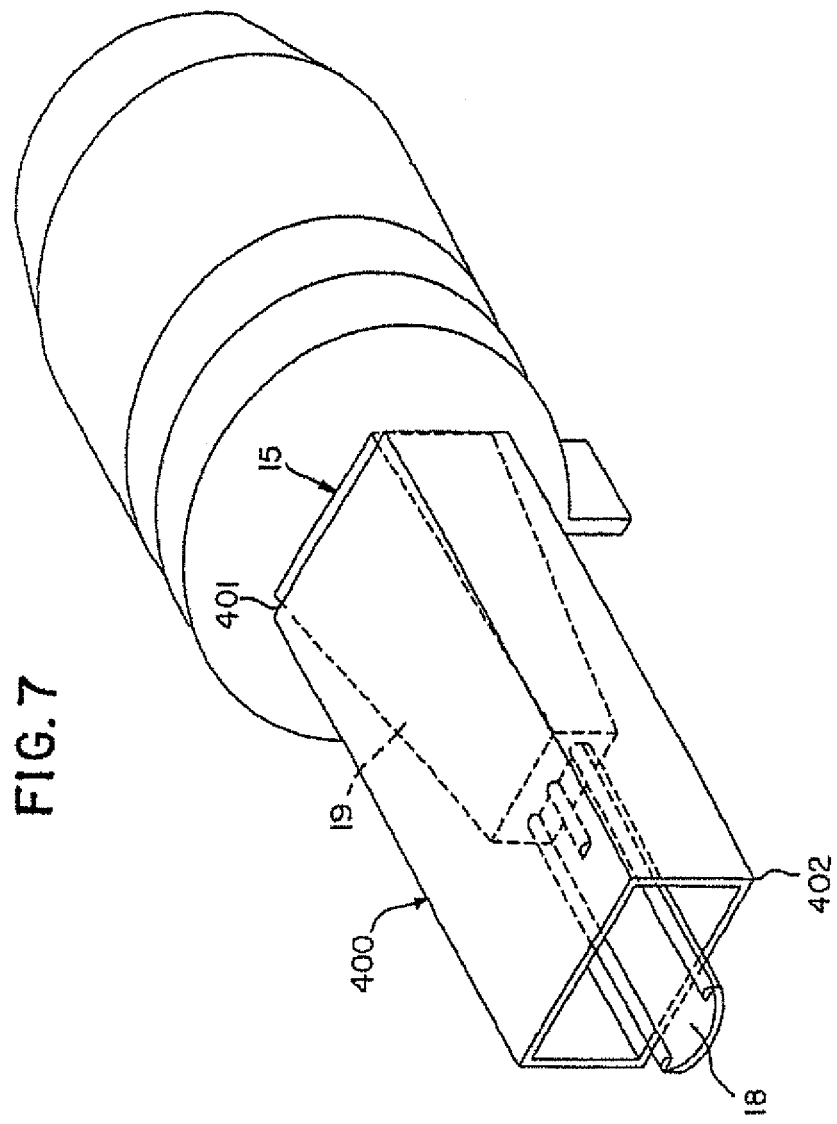
FIG. 7 is a perspective detail view of an applicator tip for use in a dispensing applicator according to the present invention having a semi-cover surrounding the frangible portion to control the speed and direction of the dispersion of the fluid in the absorbent member.

Referring to FIG. 7, there is shown an applicator tip having a semi-permeable or non-permeable cover 400 substantially surrounding frangible juncture 19. The purpose of cover 400 is to control the speed and direction of the dispersion of fluid in a surrounding absorbent member (not shown).

Preferably, a rearward edge 401 of cover 400 will be attached to applicator tip 15. More preferably, rearward edge 401 will be fully sealed around applicator tip 15 without gaps or holes so that fluid may not flow rearward under edge 401. If cover 400 is semi-permeable adjacent to rearward edge 401, fluid may flow rearward through cover 400, but preferably will not flow rearward under edge 401 given the more preferable fully sealed attachment thereof to applicator tip 15. In contrast, a forward or distal edge 402 of cover 400 is preferably free and unattached to applicator tip 15 so that fluid may flow forward under cover 400 substantially without being impeded thereby.

Preferably, cover 400 is formed as a seamless, unitary cylindrical sleeve. Nonetheless, cover 400 may be of any suitable shape and construction. Depending upon its intended function, cover 400 may be semi-permeable or impermeable to fluid. Cover 400 may be made of various materials, including natural and/or synthetic rubbers, thermoplastics (e.g., polyethylene), cellulosic materials or similar fibers (i.e., natural polymeric fibers), and metallic materials. Cover 400 may be a contiguous sheet, a mesh, a felt, or another suitable form, with or without reinforcing fibers and/or seams (i.e., "rip-stop" seams).

Preferably, cover 400 is pliable and flexible so that it does not impede deflection of tongue member 18. In other words, it is preferable that cover 400 does not hinder the breaking of frangible juncture 19.

However, surrounding frangible juncture 19 with a cover 400 having suitable thickness and/or stiffness will provide a level of reinforcement that prevents inadvertent breaking of frangible juncture 19. According, by employing a suitable thick and/or stiff cover 400, tongue member 18 may be provided without reinforcing ribs. Thus, employing cover 400 to reinforce frangible juncture 19 will advantageously simplify production of application tip 15, since tongue member 18 may be molded as a simple flat extension.

Referring again to FIG. 1, a dip mold process may be used to make source body 10, applicator tip 15, or both. The dip molding process begins with preheating of a male mold made from a material having relatively high heat capacity and coefficient of thermal conductivity. This heated mold is then placed in a fluidized bed of meltable particulate resinous material for a time needed to provide a coating of a desired thickness. The mold with melted resinous material is then removed from the fluidized bed, heated a second time and cooled. Finally the tube component is stripped from the mold.

As noted above, it is important for the proper functioning of the applicator that the tube be fabricated from a material that is sufficiently rigid to enable manual fracture of the frangible end portion. If the material is too flexible, deflection of the stem will not produce the desired result. On the other hand, if the material is excessively rigid and brittle, the possibility of an inadvertent fracture will exist, and compression of the body portion to promote flow would be precluded due to the likelihood of cracking, or simply because excess force is required. A variety of synthetic resinous materials may be utilized, the selection of which will be evident to those skilled in the art. The resin must have a sufficiently low melt viscosity to permit coverage of all mold surfaces, and it must produce a nonporous and pinhole-free structure. The polymer will normally be a thermoplastic, and exemplary materials include polypropylene, high density polyethylene, rigid polyvinyl chloride and nylon.

The tongue member of the applicator tip will preferably be elongated to facilitate attachment thereof to the absorbent member 8. However, it is not essential that the tongue member 18 be of any specific shape and, for example, may be rectangular or cylindrical. Regardless of the shape of tongue member 18, it is essential that suitable reinforcing ribs, as described hereinabove, be included to prevent unintentional breaking or separation of frangible portion 19. Moreover, the shape of tongue member 18 will dictate the shape of the orifice formed in applicator tip 15 where the tongue member 18 is fractured for fluid release. Accordingly, the flow rate and overall amount of fluid applied to an application surface by dispensing applicator 1 is a function of several factors, including the shape and strength of tongue member 18 (and the resulting orifice), the porosity of absorbent member 8, the density of the fluid, and the force employed by the user when breaking frangible portion 19 and pressing absorbent member 8 against the application surface. Determining the optimal flow rate for a given application is well within the ability of one skilled in the art and, therefore, will not be elaborated upon herein.

As stated above, the porous member may be made of any suitable material(s), most notably open cell, soft, and pliant sponge-like foam, that may be, for example, a polyurethane composition. The choice of material will depend largely upon the particular application and the characteristics of tongue member 18 and the fluid held in source body 10.

In its normal form, source body 10 will be of circular cross-section. However, other shapes are also believed to be feasible. The source body 10 may have a square, triangular, or rectangular cross-section, and the shape may indeed be asymmetrical in cross section and of dissimilar shapes at different points along its length. It will be appreciated therefore that, as used herein the term "diameter" is to be construed in a broad sense, so as to be applicable to non-circular elements corresponding to those shown, and to refer to the maximum cross-sectional dimension of the element. Although normally completely hollow, the source body 10 may include appropriate reinforcement elements, such as internal support pillars, to provide adequate overall strength and rigidity, while permitting the source body 10 to have a thinner than would otherwise be possible. Likewise, source body 10 may include a solid portion, for example, to be gripped while breaking frangible portion 19, so that source body 10 will not be prematurely compressed or squeezed, which might result in too much fluid flowing too quickly into absorbent member 8.

Figure 8:
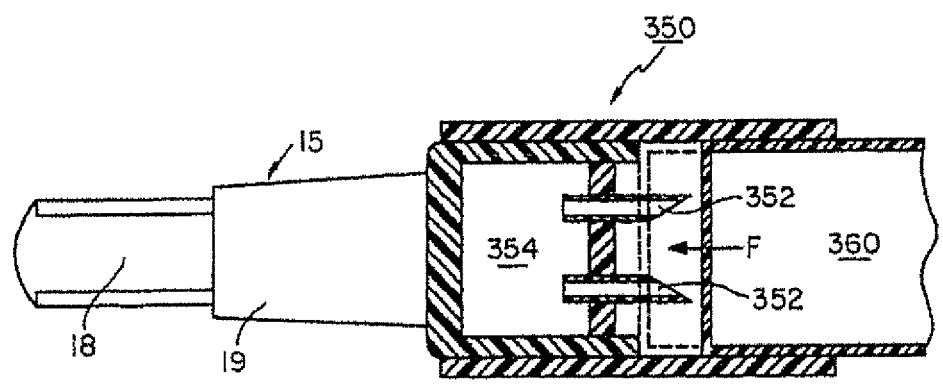
FIG. 8 is a side cross-sectional view of a further aspect of an embodiment of an applicator according to the present invention.

Controlling a rate of dispensing fluid is critical because a) over saturation of the absorbent member reduces the collecting capability of this member, and b) back flow of the delivered fluid from the distal end towards the proximal end of the absorbent member interferes with the physician's work. Accordingly, FIG. 8 illustrates a further embodiment of the invention directed to a dispensing applicator 350 which is configured to prevent fluid from uncontrollably entering an attachment member 354 that is coupled to tip 15. At least one, but preferably a multiplicity of capillary vessels 352 is provided within the attachment member. Being in fluid communication with a source body 360, vessels 352, by virtue of their cross-section, meter an amount of fluid penetrating into the absorbent member (not shown). Thus, a combination of the openings, which are formed as a result of breaking frangible region 19 and vessels 352, effectively limits oversaturation of the absorbent member.

Figure 9:
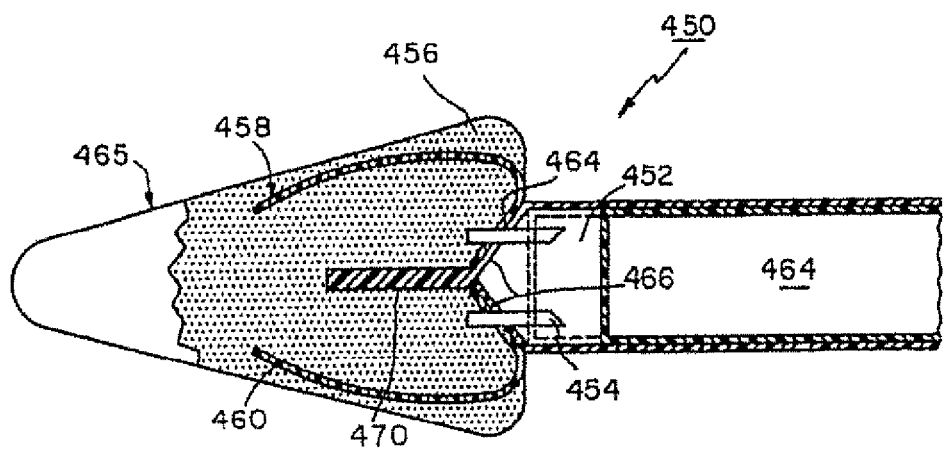
FIG. 9 is a side cross-sectional view of another aspect of an embodiment of the dispensing applicator configured with a collecting and guiding means for minimizing unintended evacuation of fluid via a proximal end of a fluid absorbent member enabling a preferred directional fluid flow.

Still another embodiment of a dispensing applicator 450 is illustrated in FIG. 9. As shown, applicator 450 does not have a frangible structure or region. Instead, an attachment member 452 is provided with at least one or more capillary vessels 454 controllably traversed by fluid from fluid source 464. Vessels 454 project into an applicator tip 465 while penetrating a proximal end of an absorbent member 456. The cross-section of the vessels is selected to provide a metered delivery of fluid.

However, absorbent member 456 can still accumulate an excessive amount of fluid, which will eventually result in a backflow towards the proximal end of the absorbent member and subsequent voluntary evacuation of fluid via this end. To limit or minimize such a possibility, applicator 450 has a flow limiting component or cover 458. Formed within absorbent member 456 and, preferably, sealed to the proximal end thereof, cover 458 is able to collect fluid flowing towards the proximal end of absorbent member 456 and, thus, prevents uncontrollable evacuation of accumulated fluid.

As illustrated, cover 458 is provided with a body having a pair of concave sides 460 whose free or distal ends are spaced from one another at a distance that defines an open exit/entrance for fluid. The bottom portions 464 of cover 458 extend complementary to converging flanks 466 of attachment member 452. Stability of an applicator tip 465 is added by providing the distal end of attachment member 452 with a rib 470. Note that cover 458 does not completely prevent backflow of fluid leaving a space within the absorbent member which is sufficient to amply, but not excessively, wet the surfaces of this member.

Figure 10A:
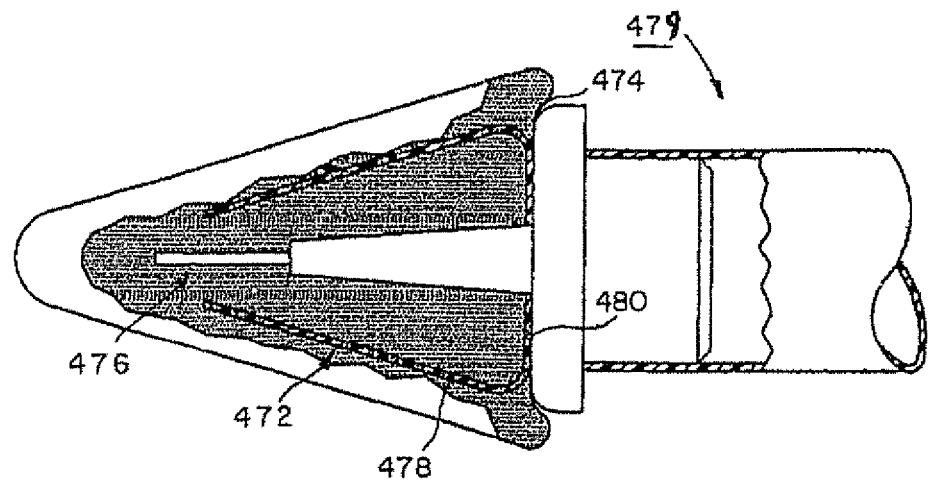
FIGS. 10A and 10B are side sectional and rear sectional views of still another embodiment of the present invention.
Figure 10B:
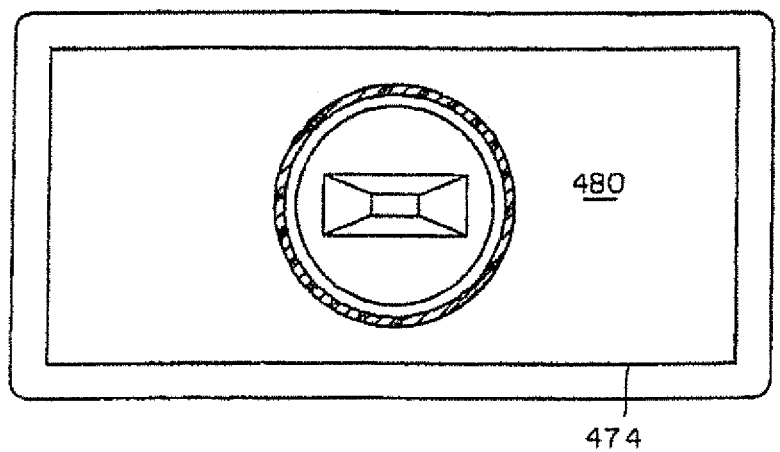

A further embodiment of dispensing applicator 479 is illustrated in FIGS. 10A and 10B. Applicator 479 has a frangible region 19 structured substantially similar to the like configured regions which are discussed in detail above. To prevent uncontrollable evacuation of fluid via a proximal end 474 of an absorbent member 476, applicator 479 has a cover 472 functioning similarly to cover 458 of FIG. 9. However, cover 472 is configured with a pair of rectilinear flanks 478 and a bottom portion 480 that extends parallel to a flat distal end of attachment member.

The applicator 479 is formed by inserting cover 472 into and sealing it to the interior of absorbent member 476. The bottom portion 480 lies preferable flush with the proximal end of the absorbent member and is sealingly attached to frangible region 19.

Embodiments of a dispensing applicator 490 illustrated in FIGS. 11A and 11*b* are conceptually close to the embodiment illustrated in FIGS. 5A and 5B and include an applicator head 492 which is formed with an absorbent member 494 and a swab member 496. The absorbent and swab members have a center axes A-A and B-B, respectively, which intersect one another forming an angle of about 80-100°.

The difference between the embodiment of FIGS. 5A and 5B and the current one includes utilization of one or more capillary vessels 498 provided instead of the frangible region. While, swab member 496 of FIG. 11A is prevented from fluid communication with an interior of a fluid source body, swab member 496 of FIG. 11B is traversed by a capillary tube 499 and has an inner surface 497 in fluid communication with the interior via an opening 495, for the reasons explained above in reference to FIGS. 5A and 5B.

The present invention is primarily directed to a dispensing applicator for the application of liquids to the surface of the head, limbs, and/or body for medical purposes (i.e., presurgical disinfection). However, dispensing applicators according to the present invention may be used in a wide variety of purposes and environments. For example, a dispensing applicator according to the present invention can be used for application of lubricant(s) or adhesive(s). The range of sizes can also vary widely, as long as the several wall thicknesses are controlled appropriately to afford the desired functional characteristics discussed herein. It should also be appreciated by those of skill in the art that the fluid reservoirs, in selected embodiments, are flexibly bounded and allow an operator to control volumetric application based on the amount of pressure applied to the exterior of the reservoir. As a consequence of this design, it should also be recognized by those of skill in the art, that an operator releasing a compressed reservoirs, may partially suction released fluid back into the reservoir and minimize pooling.

Another embodiment of the dispenser is depicted in FIGS. 12-27. With reference to those Figures, dispensing applicator 60 comprises a mounting block 66 having a base piece 61, a bottom side skirt part 62 to which is affixed an absorbent sponge type applicator 63, and a stem piece 64 upstanding from base piece 61. An absorbent swab 65 is carried at an adjacent side of the mounting block 66, for which purpose the mounting block 66 includes a mounting bracket 67 (depicted to advantage in FIG. 18) receptive of a skirt piece 68 to which swab 65 is affixed.

Stem piece 64 is a tubular component and its interior space is in communication with the interior space 69 of base piece 61, the last mentioned space outletting to absorbent applicator 63 so that a flow course in the mounting block 66 has inlet in the stem piece 64 and outlet at applicator 63. An elongated fluid container 70 is attachable to the mounting block, an end of the container being received in stem piece 64.

Referring in more detail to FIGS. 12-17, container 70 which is of tubular configuration is capped at a first end as at 71. At a distal opposite end length, an attachment member 72 has a length portion, as at 73, received inside the container; and, the length portion is affixed to the container as, for example, by heat sealing. The length portion has a flange 80 thereon and a continuing length portion 73*a* constituting a frangible section, this section transitions into a tongue element, 74. The juncture of the tongue element 74 and the continuing length portion 73*a* defines a weakened joinder location at which the fracture and at least partial separation of the tongue element from the frangible section will occur, enabling outletting of fluid from container 70.

Figures 14, 15, 16, 17:
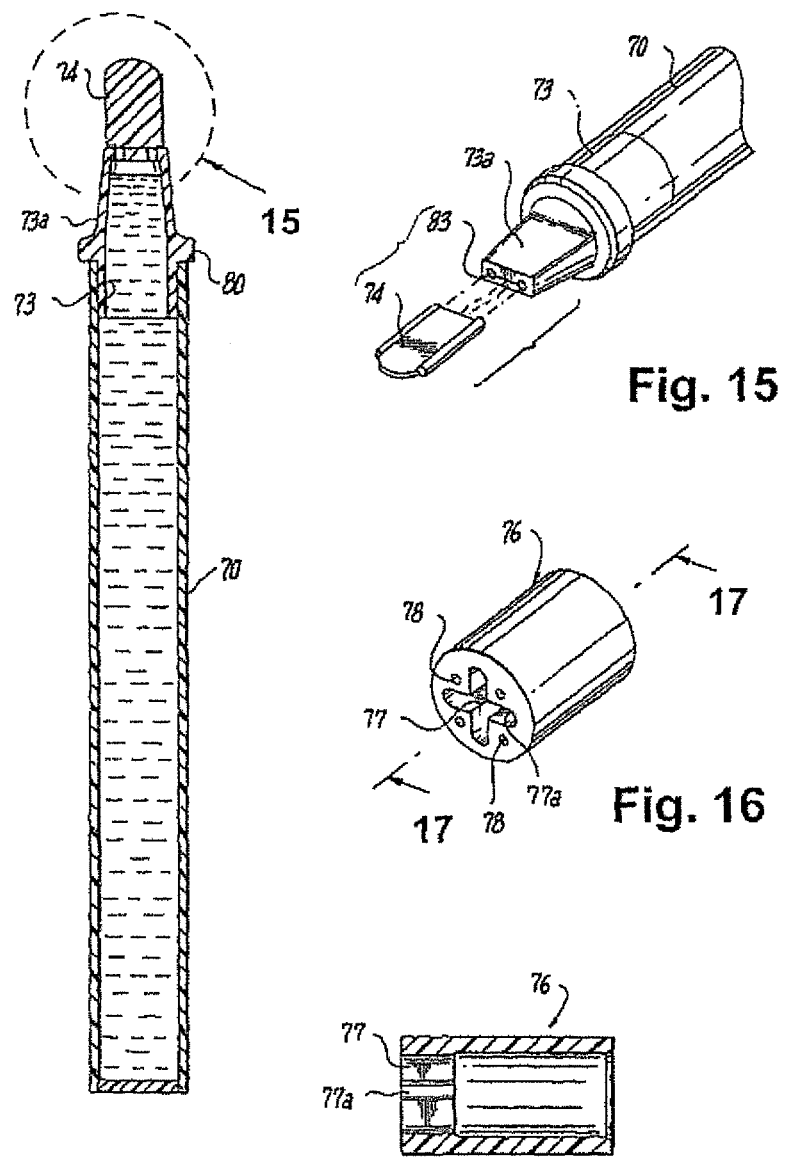
FIG. 14 is a plan view in section of the fluid source container, the container being closed at one end, an attachment body being located remote from said container one end, a frangible length region including a tongue element extending longitudinally from said attachment body.
FIG. 15 is a fragmentary perspective view of the applicator portion in the circle area 15 of FIG. 14, the tongue element being separated a distance from the attachment body frangible region so that the fluid container contents outflow apertures produced when the tongue element is fractured from the frangible length can be seen.
FIG. 16 is a perspective view of the circle area 16 in FIG. 13 of a fracture anvil removably inserted in an applicator mounting block part of the applicator head, the fracture anvil having a cruciform passage for reception of the fluid source container tongue element, the fracture anvil being employed to effect fracture of the frangible region-tongue element joinder on a relative rotatable movement between said container and said fracture anvil.
FIG. 17 is a sectional view taken on the line 17-17 in FIG. 16.

FIGS. 16 and 17 depict one embodiment of a fracture anvil 76. The fracture anvil has a cruciform passage 77 extending therethrough, as well as a number of fluid pass-through passages 78 for enabling fluid released on fracture to flow toward absorbent applicator 63.

When the second opposite end of the container 70 is inserted into the stem piece 64, the tongue element is aligned such that it will enter and locate in the cross passage part 77*a* of cruciform passage 77, the fracture anvil having been inserted in the bore of the stem piece. The second opposite end of the container 70 is snap fit connected to the stem piece 64. The arrangement is such that with flange 80 received in annular internal groove or slot 154 in the stem piece, the tongue element 74 is properly positioned in cross passage part 77*a* for effecting fracture (FIG. 21).

External dimensioning of the annular flange 80 and internal groove 154 is such that the container 70 can be rotated relative to the fracture anvil while the fracture anvil is held. This approximately ninety degree rotation of the container is effective to twist the tongue element 74 at the weakened joinder location with length portion 73a, fracturing it and effecting at least partial separation from length portion 73a. With this fracture, fluid releases from the container into the mounting block through course. FIGS. 21, 22 and FIGS. 23, 24 show, respectively, pre and post-fracture orientations of length portion 73a.

FIG. 25 shows how fluid outlets the container in streams from apertures 83 at the fracture site of tongue element 74 and length portion 73a, the apertures 83 being shown in FIG. 15 as well. FIG. 26 shows the pattern of fluid flow to and distributed throughout the absorbent applicator 63, which distribution is promoted by the passages 84 formed in the applicator 63.

Figure 27:
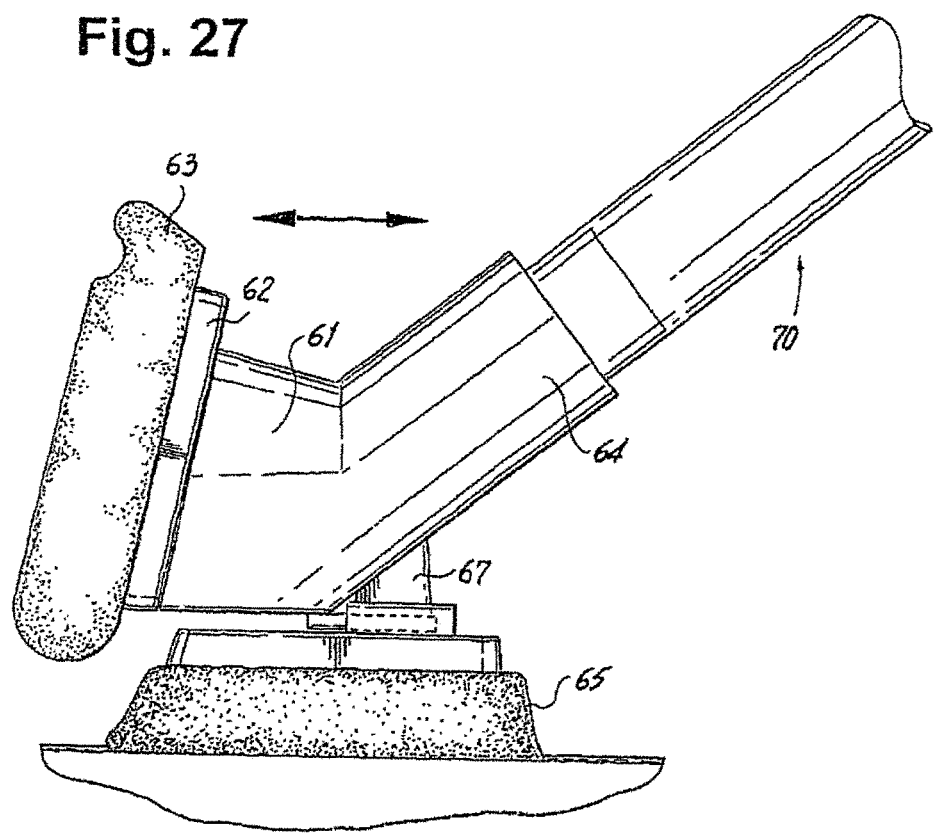
FIG. 27 is a left side elevation view of the applicator dispenser depicting the orientation of the mounting block to present an absorbent swab to a use position.

FIG. 27 illustrates the orientation of the dispenser when, e.g., it is desired to swab a large patient area, spreading out the quantity of fluid applied to the patient with absorbent swab 65.

Figures 32, 33, 34:
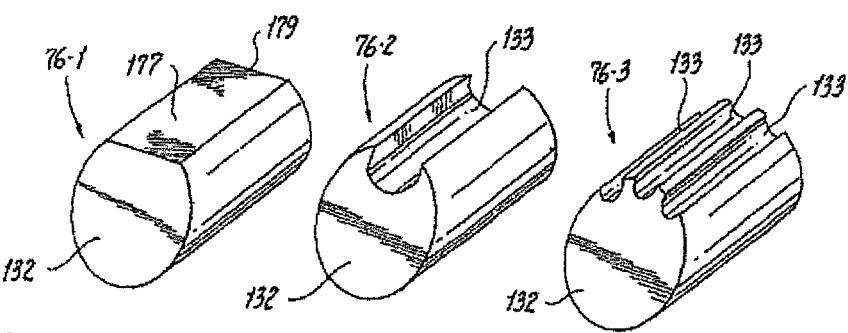
FIG. 32 is a perspective view of the circle 32 of FIG. 28, depicting detail of a first form of truncated cylindrical fracture anvil wherein a flat chord face is formed in the anvil cylindrical periphery to define with an inner encircling wall face of the stem piece, a flow channel in the mounting block through which the fluid contents communicate from the ruptured container to the absorbent applicator.
FIG. 33 is a perspective view of a second form of fracture anvil is provided with a gutter-like fluid contents flow channel at its cylindrical periphery.
FIG. 34 is a perspective view of a third form of fracture anvil wherein its periphery is provided with plural flow gutters.
Figure 35:
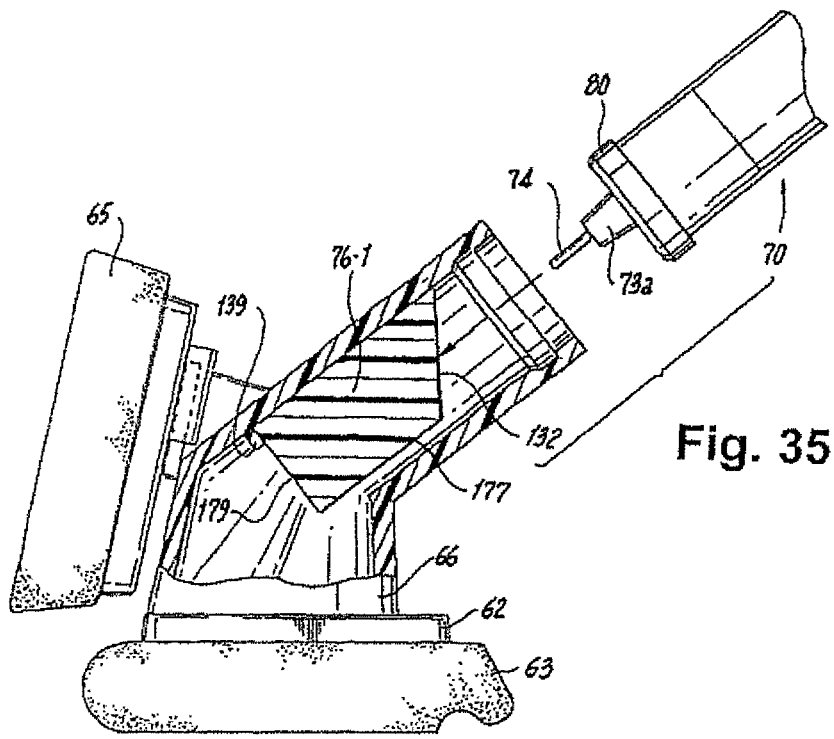
FIGS. 35-37 are a side view partly in section of the applicator showing the urging direction travel of the container to engage the tongue element against the inclined end fracture face of the fracture anvil to effect fracture of the tongue element at its joinder to the frangible section, the moved fractured position of the tongue element being depicted in dashed lines, and the release of fluid flow about the securely retained but fractured section.

FIG. 28 depicts an embodiment of dispensing applicator 60-2, which is identical with the FIG. 13 applicator 60 except wherein fracture anvil 76-1 is embodied as a truncated cylinder. The anvil 76-1 shown in more detail in FIGS. 32 and 35 is provided with a flat inclined top face 132, and with a flat chord face 177 at the cylindrical periphery thereof and extending between top face 132 and a bottom face 179. With the anvil 76-1 received in stem piece 64 as shown in FIGS. 35-37, flat chord face 177 is disposed spaced from the cylindrical inner surface of the stem piece 64 and therewith defines a flow channel along which fluid contents of container 70 can flow from interior space 99 of the stem piece 64 to the interior space 69 of base piece 61.

Figure 36:
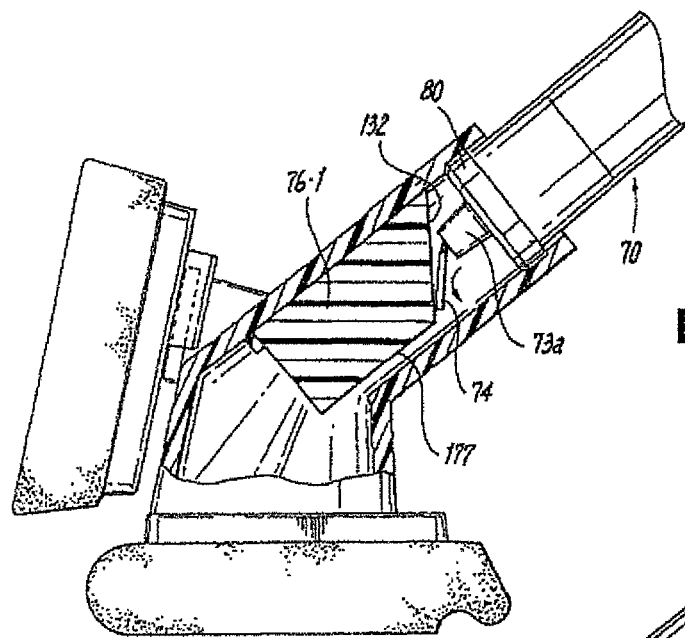
Figure 37:
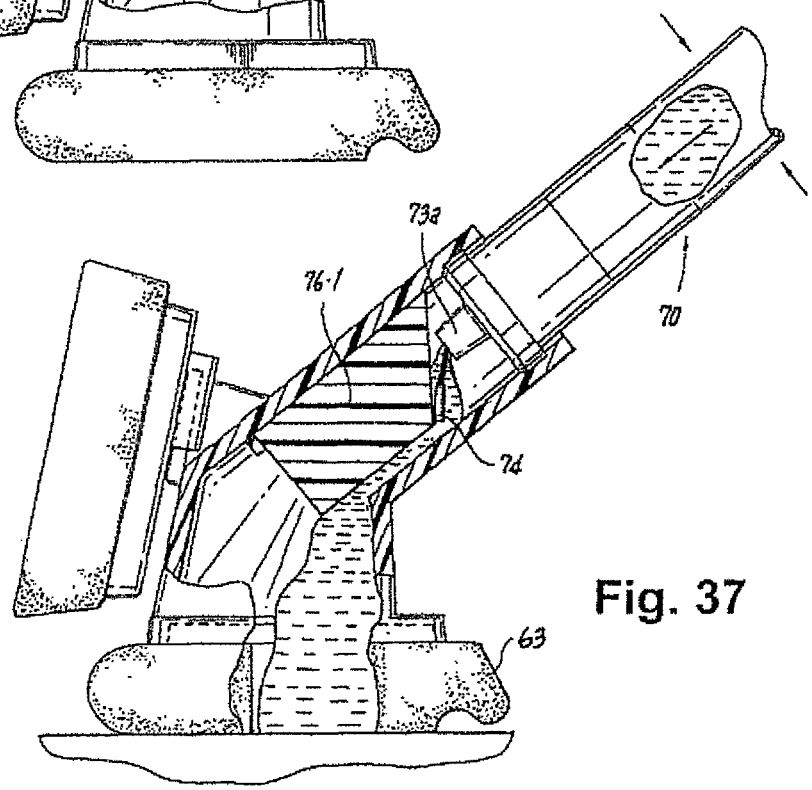

Referring to FIGS. 35-37, explanation of fracturing for fluid flow (but not separation) of the frangible weakened joint at which the tongue element 74 is connected to the frangible length part 73a is now given. The circular inner surface of the stem piece 64 is shouldered or provided with a stop as at 139 to hold the fracture anvil 76-1 (FIG. 32) in stopped position so it cannot move lower in the stem piece passage. When the applicator is to be used, a fluid container 70 will be inserted into the stem piece 64, tongue element 74 first. The tip end of the tongue element 74 will in course of insertion travel strike against the inclined top face 132 of the fracture anvil 76-1 in consequence of which the tongue element 74 will be laterally displaced from the full line position thereof in FIG. 35 to the position as shown in FIGS. 36 and 37. That displacement effects rupture (but not separation) of the tongue element at its joinder location with the frangible region and container fluid contents are released through orifices 83 (FIG. 15) into the stem piece interior space. It is specifically noted, that in FIG. 31 the separation is shown only for purposes of visualizing the openings accessed by fracture of the frangible regions, and it will be recognized that the inner joining region of tongue member 74 remains firmly and securely attached to head member 80, and is merely displaced allowing a fluid-flow access to the openings noted. Thus, FIG. 31 is for illustrative purposes only and does not reflect a separation.

Additional fracture anvil embodiments are shown in FIGS. 33 and 34. In these embodiments, the truncated cylinder anvils 76-2 and 76-3 unlike fracture anvil 76-1, retain their outer surface cylindrical envelopes. Like fracture anvil 76-1, these anvils each have an inclined flat top face 132 and a flat bottom face 179. To provide flow from the inclined top face to the flat bottom face side of the fracture anvils, gutter-like flow channels 133 are formed in the cylindrical periphery of each anvil, these flow channels 133 extending from the inclined top face 132 to the flat bottom face 179. Fracture anvil 76-2 has one flow channel or relatively large cross section area, whereas, fracture anvil 76-3 has plural, i.e., three flow channels each of smaller cross section area but in total about the same as the cross section area of fracture anvil 76-2. The flow channels 133 juxtapose with the inner encircling periphery of the stem piece and provide ample artery volume to insure proper fluid flow to the absorbent applicator 63

An important consideration in the dispensing applicator is (a) complete filling of container 70 during manufacture to ensure maximum supply and (b) avoidance of contamination of the fluid contents in the container 70 both as to at initial filling of disinfectant and medicaments therein and as to post filling handling and storage until need to use. It will be recognized by those of skill in the art, that achieving (a) will eliminate air pockets prior to use that will impact contamination in (b). In this regard and with continuing reference to FIGS. 29 and 30, the container 70 of dispensing applicator 60-2 is provided at its first or filling end with a capping assembly 240 (as shown) that includes a closure cap 241 having a central disc part 243 and an axially directed peripheral skirt 242 encircling the outer surface of the container 70 at its first end. The first end tip part of container 70 has a radially inwardly directed annular flange 244 defining a central opening 245 (See FIG. 30) in the container tip end. A boss 248 projects axially from the inner face of central disc part 243 and with the cap in place on the container first end, the boss 248 will locate a distance through central opening 245 upon assembly. The capping assembly also includes a, e.g., foil material gasket 250 constructed from a suitable material which is used to intervene the inner side of the closure cap 241 and the first end face, i.e., the annular flange 244 outer face of the container 70.

FIG. 30 depicts the manner of container filling. A filling line 252 (shown as a tube) in the sterile filling operation environment delivers disinfectant or medicament fluid as discussed herein of any suitable kind through central opening 245 into the container until there is overflow of fluid at which point the filling is terminated. Gasket 250 is then set on top of the outer face of flange 244, the gasket being of larger area expanse than flange 244 and makes liquid contact for sealing purposes. Further, gasket 250 is selected from materials which are liquid proof, stretchable or deformable to a certain degree so that when closure cap 241 is fitted over the first end of the container sandwiched between the closure cap inner face and the outer face of flange 244, an air tight joint seal of the container is effected without a bubble, since the gasket material will conform to the sandwiching structure in intimate contact therewith. FIG. 29 illustrates this clearly and employs a formed main tube body 70 having only smaller opening 245. It is also to be noted from FIG. 29 that fluid fills the first end of the container 70 and is in air excluding contact with the gasket, and the apparent fluid gap in FIG. 29 is employed only to show depth of the fluid and not the existence of an unfilled portion of the tube. This arrangement assures absence of any possible contaminants-containing air within the container. It is preferred that the closure cap 241 once in place be not removable from the container. This can be effected by sonic welding or other attachment means of the closure cap to the container and optionally of the foil closure itself. If it is thought expedient for any reason, the cap can be removably snap fitted to the container. For example, an annular groove in one of the structure inner skirt surface and outer surface of the container, and an annular bead on the other of said surfaces will allow removal the closure cap but only with deliberately intended such action.

In the claims, means- or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

It will be understood that the present invention may be embodied in other specific forms without departing from the spirit or central characteristics thereof. The present examples and embodiments, therefore, are to be considered in all respects as illustrative and not restrictive, and the invention is not to be limited to the details given herein.

What is claimed is:

1. A dispensing applicator, comprising:
   a tubular container configured to contain a fluid, the container including an inlet end and an outlet end;
   a cap secured to the inlet end of the container; and
   a gasket placed between the inlet end and the cap,
   wherein the cap is configured to deform without rupturing the gasket such that the gasket fills any void remaining within the container after the container is filled with a predetermined volume of the fluid, and wherein the container is compressible when the outlet end is opened such that the container is transition able between a first state in which the container has a first volume and a second state in which the container has a second volume, the second volume being smaller than the first volume, the container being biased toward the first state and transitions to the second state upon compressing the container.

2. The dispensing applicator of claim 1, wherein the container has a length and a first width that is generally uniform along the length of the container, the inlet end defining an opening that has a second width, the second width being smaller than the first width.

3. The dispensing applicator of claim 2, wherein the second width is substantially smaller than the first width.

4. The dispensing applicator of claim 2, wherein the opening of the inlet end is configured to receive a filling line for delivering fluid through the opening into the container, the inlet end being substantially closed when the filling line is placed within the opening.

5. The dispensing applicator of claim 1, wherein the gasket is formed from a foil material.

6. The dispensing applicator of claim 1, wherein the cap is permanently secured to the container.

7. The dispensing application of claim 6, wherein the cap is sonically welded to the container.

8. The dispensing applicator of claim 1, wherein the cap is snap fitted to the container.

9. The dispensing applicator of claim 1, wherein the container comprises a head member at the outlet end, the head member including a frangible region and further comprising:
   a substantially rigid tongue extending longitudinally through the frangible region; and
   a fracture anvil engaged with the rigid tongue element and configured to fracture the frangible region without entirely separating the tongue from the head member.

10. The dispensing applicator of claim 9, wherein the fracture anvil comprises;
    one or more gutter flow channels formed in a periphery of the fracture anvil, the gutter flow channels being configured to direct a flow of the fluid.

11. The dispensing applicator of claim 9, wherein relative axial movement of the fracture anvil and the tongue causes the frangible region to fracture.

12. The dispensing applicator of claim 9, wherein relative rotational movement of the fracture anvil and the tongue causes the frangible region to fracture.

13. The dispensing applicator of claim 12, wherein a rate of flow of the fluid from the applicator corresponds to a number of degrees of relative rotation between the fracture anvil and the tongue.

14. A dispensing applicator, comprising:
    a tubular container configured to contain a fluid, the container including an inlet end and an outlet end, the container including a head member at the outlet end, the head member including a frangible region;
    a substantially rigid tongue extending longitudinally through the frangible region; and
    a fracture anvil engaged with the rigid tongue element and configured to fracture the frangible region without entirely separating the tongue from the head member,
    a cap secured to the inlet end of the container; and
    a gasket placed between the inlet end and the cap,
    wherein the cap is configured to deform the gasket such that the gasket fills any void remaining within the container after the container is filled with a predetermined volume of the fluid.

15. The dispensing applicator of claim 14, further comprising:
    a stem piece fluidically coupled to the head member, the stem piece including a mounting block; and
    one or more absorbent swabs coupled to the mounting block.

16. The dispensing applicator of claim 15, wherein the fluid flows to at least one of the absorbent swabs upon compression of the container.

17. The dispensing applicator of claim 15, wherein at least one of the absorbent swabs are removably coupled to the mounting block via a mating connection.

18. A dispensing applicator, comprising:
    a tubular container configured to contain a fluid, the container including an inlet end and an outlet end;
    a cap secured to the inlet end of the container; and
    a gasket placed between the inlet end and the cap,
    wherein the cap is configured to deform without rupturing the gasket such that the gasket fills any void remaining within the container after the container is filled with a predetermined volume of the fluid.

19. The dispensing applicator of claim 18, wherein the cap includes a central disc part and a boss that projects axially from the central disc part.

20. The dispensing applicator of claim 19, wherein the cap includes an opening extending therethrough and the boss extends a distance through the opening when the cap is secured to the container.

* * * * *